United States Patent
Hung et al.

(10) Patent No.: US 6,638,727 B1
(45) Date of Patent: Oct. 28, 2003

(54) METHODS FOR IDENTIFYING TREATING OR MONITORING ASYMPTOMATIC PATIENTS FOR RISK REDUCTION OR THERAPEUTIC TREATMENT OF BREAST CANCER

(75) Inventors: David T. Hung, Belmont, CA (US); Susan Love, Pacific Palisades, CA (US)

(73) Assignee: Cytyc Health Corporation, Boxborough, MA (US)

( * ) Notice: Subject to any disclaimer, the term of this patent is extended or adjusted under 35 U.S.C. 154(b) by 0 days.

(21) Appl. No.: 09/313,463

(22) Filed: May 17, 1999

Related U.S. Application Data

(60) Provisional application No. 60/117,281, filed on Jan. 26, 1999.

(51) Int. Cl.$^7$ .............................................. G01N 33/574

(52) U.S. Cl. ..................... 435/7.23; 424/195.1; 435/7.2; 435/7.1; 435/7.4; 436/63; 436/64; 436/501; 436/503

(58) Field of Search ....................... 424/195.1; 435/7.23, 435/7.1, 7.2, 7.4; 436/63, 64, 501, 503; 514/176, 317, 319, 324, 648

(56) References Cited

U.S. PATENT DOCUMENTS

| | | |
|---|---|---|
| 3,608,540 A | 9/1971 | Sartorius |
| 3,786,801 A | 1/1974 | Sartorius |
| 4,202,329 A | 5/1980 | Kortum |
| 4,365,632 A | 12/1982 | Kortum |
| 4,981,692 A | 1/1991 | Popescu et al. |
| 5,279,608 A | 1/1994 | Cherif Cheikh |
| 5,478,556 A | 12/1995 | Elliott et al. |
| 5,518,885 A | 5/1996 | Raziuddin et al. |
| 5,527,528 A | 6/1996 | Allen et al. |
| 5,531,736 A | 7/1996 | Wong et al. |
| 5,763,415 A | 6/1998 | Sukumar |
| 5,798,266 A | 8/1998 | Quay et al. |
| 5,801,021 A * | 9/1998 | Gray et al. ................. 435/94.2 |
| 5,840,059 A | 11/1998 | March et al. |
| 5,914,238 A | 6/1999 | Keesee et al. |

FOREIGN PATENT DOCUMENTS

WO    WO 97/05898    2/1997

OTHER PUBLICATIONS

Petrakis, Cancer Epidemiology, Biomarkers, and Prevention, 3:3–10, Feb. 1993.*
King et al. Journal of the National Cancer Institute 71/6:1115–1121, Dec. 1983.*
Grese et al. Current Pharmaceitucal Design 4:71–92, 1998.*
Azavedo et al. Anticancer Research 6:263–266, 1986.*
Zhang et al. Chinese Journal of Clinical Oncology 23/6:381–385, 1996.*
Hou et al, Radiology vol. 195 p. 568 (1995).*
Fisher et al., "Tamoxifen for prevention of breast cancer: Report of the National Surgical Adjuvant breast and bowel project P–1 study" Journal of the National Cancer Institute (1998) 90(18):1371–1388.
Goodson et al., "Discharges and secretions of the nipple" The Breast: Comprehensive Management of Benign & Malignant Diseases, Bland & Kirby, Eds., W.B. Saunders, Philadelphia, Second Edition, Chapter 4, (1998) 2:51–74.
King et al., "Nipple aspirate cytology for the study of breast cancer precursors" Journal of the National Cancer Institute (1983) 71:1115–1121.
Love et al., "Breast–duct endoscopy to study stages of breast cancerous breast disease" The Lancer (1996) 348:997–999.
Papaicolaou et al., Exfoliative cytology of the human mammary gland and its value in the diagnosis of cancer and other diseases of the breast: Cancer (1958) 11(2):377–409.
Sartorius et al., "Cytologic evaluation of breast fluid in the detection of breast disease" Journal of the National Cancer Institute (1977) 59(4):1073–1078.
Sauter et al., "Nipple aspirate fluid: A promising non–invasive method to identify cellular markers of breast cancer risk" British Journal of Cancer (1997) 76(4):494–501.
Wrensch et al., "Breast cancer incidence in women with abnormal cytology in nipple aspirates of breast fluid" American Journal of Epidemiology (1992) 135(2):130–141.
Arteaga et al, J Nat Cancer Inst. Jan. 6, 199; vol. 91 No. 1:46–53.
Barnes & Masood. "Potential value of hormone receptor assayin carcinoma in situ of breast" Am J. Cancer Prevention 11/90.
Berntsen, et al. "Influence of Treatment with Aminoglutethimide on Plasma and Red–Blood–Cell Glutathione Status in Breast Cancer Patients." Cancer Chemother Pharmacol. 1998. vol. 42, pp. 46–52.
Boccuzzi, et al., "Breast Duct Fluid Dehydroepiandrosterone sulphate in Fibrocystic Disease." European J. Cancer and Clinical Oncology. Aug. 1987. vol. 23, pp. 1099–1102.
Buzdar, J Clin Oncol. 1998; Jan. 16(1): 348–53.
"Cancer detection techniques shown." Santa Barbara News Press Aug. 3, 1971.
Cassels, "New test may speed breast cancer detection." The Medical Post Mar. 20, 1973.
Ernster, et al. "Benign and malignant breast disease: initial study results of serum and breast fluid analyses of endogenous estrogens." J. Nat. Cancer Inst. vol. 79 No. 5.
Fabian, et al., "Biomarker and cytologic abnormalities in women at high and low risk for breast cancer" J. of Cellular Biochemistry 17G:153–160 (1993).

(List continued on next page.)

*Primary Examiner*—Sheela Huff

(57) ABSTRACT

The invention is to methods for identifying asymptomatic patients who have a likelihood of benefiting from administration of an estrogen activity modulator for risk reduction or therapeutic treatment of breast cancer, methods for reducing risk or therapeutically treating these asymptomatic patients, and methods for monitoring the treatments.

27 Claims, No Drawings

OTHER PUBLICATIONS

Fabian, et al. "Prevalence of abnormal biomarkers in fine needle breast aspirates in high risk populations." 1993 Proc. Ann Meeting Am Assoc. Cancer Res. 34: Abstract 1556.

Fabian, "Who should receive which selective estrogen receptor modulator for prevention of breast cancer" The Breast Journal voll 5, No. 3, 1999 211–214.

"Finding asymptomatic breast cancer." Medical World News Jul. 23, 1971.

Fryckberg, et al. "Ductal carcinoma in situ of the breast. Surgery" Gynecology & Obstetrics 10/93 vol. 177.

Head, et al. "Assessment of immulogic competence and host reactivity against tumor antigens in breast cancer with vaccines." vol. 690 of the Annals of the NY Academy of Sciences Aug. 12, 1993.

Imayama, et al. "Presence of elevated carcinoembryonic antigen on absorbent disks applied to nipple are of breast carcinoma patients." Cancer Sep. 15, 1996 vol. 78 No. 6.

"Breast Fluid cells help in early cancer detection" JAMA May 7, 1973; vol. 224, No. 6 pp. 823–827.

Osborne, New England J. Med. 1998; vol. 339, No. 22: 1609–1618.

King, et al. "Cellular composition of the nipple aspirate specimen of breast fluid." AJCP vol. 64 Dec. 1975 pp. 728–738.

Kristensen, et al. "A rare CYP19 (aromatase) variant may increase the risk of breast cancer." Pharmacogenetics. 1998. vol. 8, pp. 43–48.

Lobsenz. "A new way to detect breast cancer early." Good House Keeping Jan. 1975.

Lu et al. "The Effects of Aromatase Inhibitors and Antiestrogens in the Nude Mouse Model." Breast Cancer Research and Treatment 1998. vol. 50, pp. 63–71.

Masood & Johnson, "The value of imprint cytology in cytochemocal detection of steroid hormone receptors in breast cancer." AJCP vol. 87 No. 1 pp. 30–36.

Masood et al. Breast Health Challenges and Promises. J. Florida M.A. Aug/Sep. 1996/vol. 83, No. 7 pp. 459–465.

Masood. "Fluorescent cytochemical detection of estrogen and progesterone receptors in breast fine–needle aspirates." AJCP Jan. 1991.

Masood. "The missing link: a 'pap smear' for early breast cancer detection and prevention." The Breast Journal, vol. 5 No. 1, 1999 pp. 1–2.

Nass, et al. "Breast cancer biology blossoms in the clinic." Nature Medicine vol. 4 No. 7 Jul. 1998.

Norton, L Semin Oncol. 1997: Aug 24(4) Suppl 10; S10–S–S10–10.

O'Regan et al, 1999 Am. Coll Surgeons vol. 188; No. 6 Jun. 1999:678–684.

Papanicolaou et al. "Exfoliative cytology of the human mammary gland and its value in the diagnosis of cancer and other disease of the breast." Cancer Mar.–Apr. 1958, 11(2):377–409.

Pertschuk et al. "Estrogen receptor immunochemistry in endometrial carcinoma." Gynecologic oncology 63, 28–33 (1996) pp. 28–33.

Petrakis & King. "Genetic markers and cancer epidemiology." Cancer April supp 1977 vol. 39 pp. 1861–1866.

Petrakis et al. "Epithelial dysplasia in nipple aspirates of breast fluid: association with family history and other breast cancer risk factors." JNCI vol. 68 No. 1 Jan. 1982.

Petrakis, "Nipple aspirate fluid in epidemiologic studies of breast disease." Epidemiologic reviews vol. 15 No. 1 1993.

Rose et al. "A Comparison of Serum and Breast Duct Fluid Immunoassayable prolactin and Growth Hormon Woman and the Patients with Cystic Breast Disease." Cancer, Dec. 1, 1987, vol. 60, No. 11, pp. 2761–2765.

Sartorius et al. "The Biochemistry of breast cyst fluids and duct secretions." Breast Cancer Research and Treatment 35:255–266 1995.

Sauter et al. "Prostate specific antigen levels in nipple aspirate fluid correlate with breast cancer risk" Cancer Epidemiology vol. 5, 967–970, Dec. 1996.

Strah & Love, "The in situ carcinomas of the breast." JAMWA vol. 47 No. 5 Sep./Oct. 1992.

Sukumar & McKenzie, "Breast cancer prevention strategies for the twenty first century" Molecular Medicine Today Nov. 1996.

Sukumar et al. "Independent molecular pathways in initiation and loss of hormone responsiveness of breast carcinomas." Science 22 Apr. 1988.

Tankanow, Am J Health Syst. Pharm 1998: Sep. 1 (55/17) pp. 1777–1791.

Wrensch, et al. "Breast cancer risk associated with abnormal cytology in nipple aspirates of breast fluid and prior history of breast biopsy." Am J. of Epidemiology vol. 137 No. 8 1993.

Wynder et al. "Breast Secretion in Finnish Women: a metabolic epidemiologic study," Cancer 47: 1444–1450, 1981.

Wynder et al, "Prolactin, Oestrogen, and Lipids in Breast Fluid." The Lancet 22 Oct. 1977. vol. 2 No. 8043, pp. 840–842.

Zippin & Petrakis., "Identification of high risk groups in breast cancer." Cancer vol. 28 pp. 1381–1387 Dec. 1971.

Hou et al., "A simple method of duct cannulation and localization for galactography before excision in patients with nipple discharge" Radiology (1995) 195:568–569.

Pansera, F., "Accessibility and possibility of elimination of breast epithelium: The theoretical possibility of preventing breast carcinoma through destruction of the epithelium of origin" Medical Hypothesis (1990) 33:107–111.

* cited by examiner

METHODS FOR IDENTIFYING TREATING OR MONITORING ASYMPTOMATIC PATIENTS FOR RISK REDUCTION OR THERAPEUTIC TREATMENT OF BREAST CANCER

This application claims the benefit under 37 CFR 1.78(b) of provisional application No. 60/117,281, filed on Jan. 26, 1999, the full disclosure of which is incorporated herein by reference.

BACKGROUND OF THE INVENTION

1. Field of the Invention

The field of this invention is identifying, treating and monitoring patients having breast cancer or patients at risk of getting breast cancer.

2. Description of the Background Art

Estrogen activity has an established relationship to breast cancer. Thus, drugs are presently being developed and tested that modulate estrogen activity in an attempt to treat patients having hormone responsive breast cancer. These new drugs can be classified as estrogen activity modulators. Estrogen activity modulators include estrogen receptor modulators (e.g. selective estrogen receptor modulators or SERMs), estrogen antagonists, and modulators of estrogen synthesis.

Whether estrogen activity modulators can be used for reducing the risk of or therapeutically treating breast cancer depends almost entirely on identifying a patient population that will benefit from the drug. Previously, determinations of a patient's likelihood of contracting cancer have been largely developed based on epidemiology and genetics. Tests directed to specific individuals to screen for patients at risk for contracting breast cancer have not existed. However, some patients who have precancer of the breast can be identified haphazardly by incidental or accidental detection during other procedures. See Fisher et al, (1998) *J. Nat'l Cancer Inst*, vol. 90 (18): 1371–1388 using incidental or random biopsy to identify patients having atypical ductal hyperplasia.

Patients having breast cancer are presently identified by such means as mammography, fine needle aspiration biopsy (FNAB), FNAB guided by mammography, biopsy, magnetic resonance imaging (MRI), or other standard means that may include dosing a patient with radiation or incurring tissue damage in the process of getting a tissue sample to analyze. These methods are deficient because they do not detect early cancer, cannot detect precancer, and may cause damage to patients that have cancer by disrupting tissue near and around the cancerous lesion, and may also cause a serious risk of unclean margins after lesion removal. In addition, standard methods to screen for cancer such as mammography, FNAB, and biopsy also provide frequent opportunity for an ambiguous or false result. Thus, the medical community would benefit greatly from the application of a sensitive, non-radiation based, and non-invasive identification means for breast cancer, and a method to identify breast precancer.

There is every indication that estrogen activity modulators may be most effective if administered to patients having breast pre-cancer, or to patients having very early breast cancer (i.e. breast cancers not presently routinely detectable by standard methods). Additionally, patients having cancer may be most benefited from administration of an estrogen activity modulator if the breast tissue has not been broken or disturbed to identify the cancer. It follows that a patient having breast cancer may be most optimally treated if that cancer is detected non-invasively, and thus if the cancer is not disrupted by a surgeon's tool, which risks unclean margins and exacerbation of the cancerous lesion in the duct and surrounding tissue.

A recent study of the benefits of the selective estrogen receptor modulator (SERM) tamoxifen found that tamoxifen administration benefits both patients with cancer, and patients having pre-cancer. The study showed a 49% reduction in incidence of breast cancer with administration of tamoxifen to high risk women, and that the risk of getting invasive cancer was reduced by 86% in women with a history of atypical ductal hyperplasia (ADH), a precancerous state. See Fisher et al, (1998) *J. Nat'l Cancer Inst*, vol. 90 (18): 1371–1388. Because the women with ADH were identified by accident, the problem remains how to systematically and confidently identify such women. The present invention solves this problem.

The results from the NASBP Fisher et al study may point to the future of treatment options for women having hormone responsive breast cancers. Therapeutic treatment or risk reduction of breast cancer with estrogen activity modulators may indeed reduce the mortality risk in patients having cancer or may reduce the risk of developing breast cancer in women at high risk. Such treatment protocols depend, however, on accurate, sensitive and nondisruptive identification of the patients who can benefit from the estrogen activity modulator. The invention provides such methods of identification. The invention also provides methods of treating patients so identified and for monitoring such patients who are candidates for the treatment.

In addition, because estrogen activity modulators are not benign drugs and effect an important hormone in the female life cycle (e.g. tamoxifen increases a patient's risk for other reproductive cancers, cardiac problems and other undesirable side effects (Fisher et al, (1998) *J. Nat'l Cancer Inst*, vol. 90 (18): 1371–1388)), being able to treat the patient (once identified) when the patient is most likely to respond favorably to the modulator, and thus keeping the length of the treatment time and the treatment dose at a minimum, while maximizing the benefits against a cancer or precancer, would clearly be a benefit to the patient population. The present invention provides this benefit.

3. Relevant Literature

Papanicolaou et al (1958) *Cancer*, 11:377–409 describes exfoliative cytology from spontaneous nipple discharge of the human mammary gland and its value in the diagnosis of breast cancer. Goodson W H & King E B, Chapter 4: *Discharges and Secretions of the Nipple*, The Breast: Comprehensive Management of Benign and Malignant Diseases (1998) $2^{nd}$ Ed. vol 2, Bland & Kirby eds. W.B. Saunders Co, Philadelphia, Pa. pp. 51–74 describes nipple discharge and the ways in which it has been used to characterized conditions of the breast.

Sartorius et al (1977) proposed cytologic evaluation of breast fluid for the detection of breast disease as describe in Journal of the National Cancer Institute 59(4):1073–80. Love and Barsky, (1996) *Lancet* 348(9033):997–9 demonstrated retrieval of ductal fluid by breast-duct endoscopy to study stages of cancerous breast disease.

Nipple aspirate cytology for the study of breast cancer precursors is described in King et al, (1983) *Journal of the National Cancer Institute* 71(6):1115–21. Cytological epithelial hyperplasia and atypical hyperplasia diagnosed in nipple aspirate fluid are associated with increased risk of breast cancer in a study of 2701 women as described in Wrensch et al, (1992) *Am. J. Epidemiology*, v. 135 (2): 130–141.

Nipple aspirate fluid is identified as a promising non-invasive method to identify cellular markers of breast cancer risk in Sauter et al, (1997) *British Journal of Cancer* 76(4):494–501.

A Company called Diagnostics, Inc. formed in 1968, produced devices to obtain breast ductal fluid for cytological evaluation. The devices included a nipple aspiration device to collect NAF from subjects, and catheters to retrieve ductal fluid. The devices were sold prior to May 28, 1976 for the purpose of collecting breast ductal fluid for cytological evaluation.

U.S. Pat. No. 5,763,415 to Sukumar discloses prophylactic and therapeutic methods of treating the ductal epithelium of a breast duct by treating the duct with an epithelium destroying agent, and claims a method of treating the ductal epithelium of a mammary gland prophylactically or therapeutically for cancer by ductal cannulation of a duct, and administration of a vector comprising thymidine kinase to the duct and its prodrug ganciclovir. U.S. Pat. No. 4,981,692 to Popescu et al discloses and claims a method of treating infections in an animal by administration of a therapeutically effective amount of aminoglycoside in liposome form by intramammary infusion.

U.S. Pat. No. 4,202,329 and U.S. Pat. No. 4,365,632 to Kortum disclose a process and apparatus for stimulating immune resistance by the introduction of at least one relatively small solid non-toxic substantially non-biodegradable body, having non-specific antigenic action, into each gland cistern of the udder. The continued presence of the non-specific antigenic body induces immune resistance including an increase in the number and activity of phagocytic cells in the udder, which in turn provides protection against bacterial invasion without degrading milk quality. U.S. Pat. No. 4,202,329 claims a method for inhibiting bacterial infection by use of this process and apparatus.

SUMMARY OF THE INVENTION

The invention provides a method for identifying asymptomatic patients who have a likelihood of benefiting from the administration of an estrogen activity modulator for risk reduction or therapeutic treatment of breast cancer. The method comprises providing a ductal fluid sample from at least one duct of a breast of the patient and examining the ductal fluid sample to determine the presence of precancerous or cancerous ductal epithelial cells, wherein patients determined to have the presence of either precancerous or cancerous ductal epithelial cells are considered likely to benefit from administration of an estrogen activity modulator. The precancerous ductal epithelial cells can be cells at a stage including ductal hyperplasia, atypical ductal hyperplasia (ADH), or low grade ductal carcinoma in situ (LG-DCIS); the cancerous ductal epithelial cells can be cells at a stage including high grade ductal carcinoma in situ (HG-DCIS) or invasive carcinoma.

Providing the ductal fluid sample can comprise obtaining the sample from the breast; providing the ductal fluid sample can comprise receiving a sample which had been previously obtained. The previously obtained fluid can have been obtained by nipple aspiration of the milk ducts or by ductal lavage of at least one breast milk duct. The fluid collected can be from a single duct.

Examining the ductal fluid can comprise cytological examination of ductal epithelial cells in the sample to determine whether they are precancerous or cancerous. Examining the ductal fluid can comprise detection of an estrogen receptor in the ductal epithelial cells. Examining the ductal fluid can comprise detecting the absence of TGF-$\beta$ in the ductal fluid.

The asymptomatic patients can comprise patients in a high risk group for breast cancer such as patients with a family history of breast cancer, older patients (e.g. above 40 years old), patients having at least one high risk parity factor, patients having high risk gene status, patients having at least one previous breast biopsy, patients having a previous diagnosis of breast cancer, older patients (e.g. above 35 years old) who have never been pregnant and/or had a child) or patients having any other risk factor for breast cancer. The asymptomatic patients can comprise patients who are negative in a standard cancer test or patients with inconclusive or ambiguous results from a standard cancer test.

The estrogen activity modulator can be a selective estrogen receptor modulator (SERM), an estrogen antagonist, or a modulator of estrogen synthesis. Accordingly, the estrogen activity modulator can comprise tamoxifen, raloxifene, EM 800, droloxifene, ioxdroxifene, RU 39411, RU 58668, ICI 164384, faslodex, soy, a soy isoflavone, a gonadotropin releasing hormone agonist, or an aromatase inhibitor. The soy isoflavone can be genistein or daidzein. The aromatase inhibitor can be toremifene.

The invention further provides a method of treatment. Such a method of treatment is a method for risk reduction or therapeutic treatment of an asymptomatic patient at risk for developing breast cancer. The treatment method comprises administering an estrogen activity modulator to a patient having precancerous or cancerous ductal epithelial cells in a duct of a breast of the patient. In such a situation, a determination of the presence of precancerous or cancerous ductal epithelial cells can be made from analysis of fluid comprising ductal epithelial cells that is collected from the milk duct of a breast of the patient. The fluid can be collected by nipple aspiration of the milk ducts or by ductal lavage of at least one breast milk duct. The fluid can be collected from a single duct or from two or more ducts. Whether precancerous or cancerous ductal epithelial cells are present can be determined by cytological analysis of the ductal epithelial cells. The determination can be made by detecting the presence of estrogen receptor in the ductal epithelial cells and/or by detecting the absence of TGF-$\beta$ in the ductal fluid. The determination may also be made by examining the ductal fluid for a change in a level of a marker, including such markers as carcinoma embryonic antigen (CEA), prostate specific antigen (PSA), Erb B2 antigen, gross cystic disease fluid protein-15 (GCDFP-15), or lactose dehydrogenase (LDH) in the ductal fluid. The determination may also be made by examining the ductal fluid for a chromosomal abnormality in the ductal epithelial cells.

The estrogen activity modulator can be a selective estrogen receptor modulator (SERM), an estrogen antagonist, or a modulator of estrogen synthesis. The estrogen activity modulator can include any estrogen activity modulator, including those listed or described herein.

The invention provides a method for identifying patients who have a decreased likelihood of benefiting from the administration of an estrogen activity modulator. The estrogen activity modulator is or would be administered for risk reduction or therapeutic treatment of breast cancer. The method for making such a determination comprises providing a ductal fluid sample from a breast of the patient; and examining the ductal fluid sample to determine the presence of transforming growth factor-$\beta$ (TGF-$\beta$), or the absence of estrogen receptor. The presence of TGF-$\beta$ (e.g. high levels of TGF-$\beta$) or the absence of estrogen receptor in the ductal fluid sample indicates that the patient is less likely to benefit from the administration of an estrogen activity modulator. Providing the ductal fluid sample can comprise receiving a sample which had been previously obtained. The fluid can be obtained by nipple aspiration of the milk ducts or by ductal lavage of at least one breast milk duct. The patients who are the subject of this determination can be patients who are receiving an ongoing therapy for risk reduction or treatment of breast cancer, and that therapy can comprise administration of an estrogen activity modulator. The patient can be found to have precancer or cancer of the breast, and the precancer or cancer can have been determined by examining a ductal fluid sample of the breast of the patient. The patient can have a family history of breast cancer.

The invention provides a method of intraductal treatment. The method is a method of treating an asymptomatic patient who has a likelihood of benefiting from the administration of an estrogen activity modulator for risk reduction or therapeutic treatment of breast cancer by identifying the patient as described above and herein, and administering an estrogen activity modulator intraductally. The intraductal administration can comprise a delivery means including intraductal cannulation, intraductal catheterization, intraductal delivery of a time release capsule, intraductal delivery to a lactiferous sinus of the duct, or intraductal installment of a pump for delivering the agent into the duct. The estrogen activity modulator can be any estrogen activity modulator, including those listed or described herein. Identifying the patient can comprise identifying at least one specific duct having precancerous or cancerous ductal epithelial cells. Administering the estrogen activity modulator intraductally can comprise intraductal administration to the specific duct.

The invention also provides a method of monitoring on-going therapy in a patient at risk of or suffering from breast cancer by comparing a first level of a marker measured in a ductal fluid sample taken at a first time with a second level of the marker measured in a ductal fluid sample taken at a later time. The ductal fluid samples can be retrieved from the patient by nipple aspiration or ductal lavage of at least one breast milk duct. The therapy can comprise administration of an estrogen activity modulator. The estrogen activity modulator can be a selective estrogen receptor modulator (SERM), an estrogen antagonist, or an inhibitor of estrogen synthesis. The therapy can be begun before the marker is measured or after the marker is measured. The marker can be measured periodically. The therapy can comprise administration of any estrogen activity modulator including any of the estrogen activity modulator listed or described herein. The marker can be neoplastic ductal epithelial cells, transforming growth factor-$\beta$ (TGF-$\beta$), or estrogen receptor. The marker may also be carcinoma embryonic antigen (CEA), prostate specific antigen (PSA), Erb B2 antigen, gross cystic disease fluid protein-15 (GCDFP-15), lactose dehydrogenase (LDH) in the ductal fluid or a chromosomal abnormality in the ductal epithelial cells.

Where the marker is neoplastic ductal epithelial cells, the cells can be at a stage including hyperplasia, atypical hyperplasia (ADH), low grade ductal carcinoma in situ (LG-DCIS), high grade ductal carcinoma in situ (HG-DCIS) or invasive carcinoma. During monitoring, comparing can comprise determining a change in cellular stage, an increase of a marker, or a decrease of a marker. Comparing a first marker level and a later marker level can determine whether the patient is better, worse or unchanged. When the marker is TGF-$\beta$ an increase in TGF-$\beta$ indicates that the patient is worse. When the marker is estrogen receptor a decrease in presence of estrogen receptor indicates that the patient is worse. When the marker is neoplastic cells a change in cellular stage ranging from hyperplasia to invasive carcinoma indicates that the patient is worse. The marker may also include any such markers as carcinoma embryonic antigen (CEA), prostate specific antigen (PSA), Erb B2 antigen, gross cystic disease fluid protein-15 (GCDFP-15), or lactose dehydrogenase (LDH) found in the ductal fluid, or a chromosomal abnormality in the ductal epithelial cells.

The monitoring method can further comprise recommending a treatment course including stopping the therapy, changing the drug being administered, changing the dosage of the drug being administered, and further monitoring the patient.

The invention provides also a method for analyzing ductal fluid by providing a ductal fluid sample from a breast of the patient, and examining the ductal fluid sample to identify a level or quality of a marker including transforming growth factor-$\beta$ (TGF-$\beta$), estrogen receptor or chromosomal abnormality. The method can further be practiced by, in addition, examining the ductal fluid sample to identify a level or quality of a second marker. The second marker can include carcinoma embryonic antigen (CEA), prostate specific antigen (PSA), Erb B2 antigen, gross cystic disease fluid protein-15 (GCDFP-15), lactose dehydrogenase (LDH), epidermal growth factor receptor (EGFR), or p53. Providing the ductal fluid sample can comprise obtaining the sample from the breast. Providing the ductal fluid sample can comprise receiving a sample which has been previously obtained.

The ductal fluid can be obtained by nipple aspiration of the milk ducts.

The ductal fluid can be obtained by ductal lavage of at least one breast milk duct. The ductal fluid can be collected from a single duct. Examining the ductal fluid can further comprise cytological examination of the ductal epithelial cells in the sample.

DESCRIPTION OF THE SPECIFIC EMBODIMENTS

The following preferred embodiments and examples are offered by way of illustration and not by way of limitation.

The invention provides methods of identifying otherwise asymptomatic patients who have a likelihood of benefiting from the administration of an estrogen activity modulator for risk reduction or therapeutic treatment of breast cancer. The asymptomatic patients of the invention can comprise patients in any of the many high risk groups for breast cancer. The high risk groups can include e.g. patients with a family history of breast cancer, patients of increasing age (e.g. patients 40 years of age or older), patients having at least one high risk parity factor (e.g. early start of menses, late onset of menopause, no pregnancies, or late-age pregnancy), patients having high risk gene status (e.g. patients testing positive for a mutation in brca I or brca II gene), patients having at least one previous breast biopsy (benign or otherwise), patients having a previous diagnosis of breast cancer, and patients having any other risk factor for breast cancer. Other risk factors are continually being defined and can include such considerations, as geographic location e.g. where women living in a particular region have been found to have a higher incidence of breast cancer. Diet is believed to play a role in breast cancer risk with the hypothesis that women who include more fat in their diet are more likely to develop breast cancer (see Kniget et al (1999) *Cancer Epidemiol Biomarkers Prev* 8(2):123–8). Epidemiologists and other statisticians and scientists continue to determine other risk factors involved in breast cancer, largely in an effort to establish breast cancer epidemiology and to warn persons of avoidable risks. See also Zippin and Petrakis, (Identification of high risk groups in breast cancer) *Cancer* 28(6):1381–7, 1971.

Asymptomatic patients can be patients (including either high risk patients or patients that do not fit into a high risk category) who are negative in a standard cancer test. Standard cancer tests can include, e.g. breast palpation, mammography, fine needle aspiration biopsy (FNAB), mammography-guided FNAB, biopsy, magnetic resonance imaging (MRI), and other tests that aim to visualize or find a breast lump or to retrieve cells from a lump or lesion for analysis. An asymptomatic patient can be negative on a standard cancer test and yet still have breast precancer or cancer. Such a patient may be a candidate for administration of an estrogen activity modulator because the patient is identifiable by the method of the invention. Standard cancer tests are not always sensitive enough to detect very early stage cancers that comprise lesions of a small number of cells, and standard cancer tests are not designed to detect precancer. In addition, the tissue disruption caused to cancer lesions in the breast using standard cancer tests can cause exacerbation of the cancer, something a patient would be much better off to avoid.

For mammography or palpation to identify breast cancer, a cancerous lump in the breast must be a detectable size, meaning that the cancer must be advanced enough to be detectable by mammography or touch. Thus, mammography or palpation is unable to detect early cancer. Mammography is capable of detecting microcalcifications which are believed to be formed near a cancerous lesions, however, subsequent identification of the exact location of a lesion (usually using FNAB) proves to be a challenging venture. See Masood et al (The potential value of mammographically guided fine-needle aspiration biopsy of nonpalpable breast lesions) *American Surgeon*. 55(4):226–31, 1989 and Masood S., (Fine-needle aspiration biopsy of nonpalpable breast lesions: challenges and promises) *Cancer*. 84(4):197–9, 1998.

Invasive procedures such as FNAB are deficient because the aspiration needle may not penetrate exactly to the position of a lesion, and thus the cells retrieved in the needle may not be from the lesion. With FNAB it is also difficult to tell whether the needle has reached or located the lesion, so the results of any analysis are of limited use. FNAB guided by mammography improves the chances of retrieving lesion cells, but does not guarantee success and anyway invades tissue disrupting the otherwise healthy matrix of cells surrounding the unhealthy cells.

In addition to testing negative on a standard cancer test, an asymptomatic patient may receive inconclusive or ambiguous results from a standard cancer test, such as an ambiguous X-ray picture from a mammogram, or doubt about whether cells retrieved by FNAB are cells from the lesion. Such results may leave the patient with doubts as to what to do next, with the option of waiting until a possible cancer grows, at which time the optimum time for treatment with an estrogen activity modulator may have passed.

As a result of the silence (with regard to symptoms) of precancer and early cancer, asymptomatic patients identified by the method of the invention will be those patients having precancer or cancer but who appear otherwise healthy and asymptomatic. Such patients may benefit greatly by administration of an estrogen activity modulator for risk reduction or therapeutic treatment of breast cancer. Basic research in the molecular biology of breast cancer appears to be indicating that breast cancer can be responsive to administration with some form of estrogen activity modulator. See Howell et al (1998) *Recent Results Cancer Res* 152:227–244 ("The Primary use of Endocrine Therapies") To reduce the cancer, the patient is administered an agent that blocks estrogen activity, either by modulating estrogen, its receptor, or by blocking estrogen synthesis. An estrogen activity modulator can comprise a class of agents selected from the group consisting of a selective estrogen receptor modulator (SERM), an estrogen antagonist, and a modulator of estrogen synthesis. The estrogen activity modulator can be tamoxifen, raloxifene, EM 800, droloxifene, ioxdroxifene, RU 39411, RU 58668, ICI 164384, faslodex, soy, a soy isoflavone, a gonadotropin releasing hormone agonist, or an aromatase inhibitor. The soy isoflavone can be genistein or daidzein. The aromatase inhibitor can be toremifene. Some possible candidate estrogen activity modulators are described in el Khissiin and Leclercq, (1998) *Steroids* 63(11): 565–74; O'Regan et al (1998) *J Nat'l Cancer Inst* 90(20):1552–8; Favoni and Cupis (1998) *Trends Pharmacol Sci* 19(10): 406–15; Williams, G M (1998) *J Nat'l Cancer Inst* 90:1671; Huynh et al (1996) *Clin Cancer Res* 2:2037–2042; England and Jordan (1997) *Oncol Res* 9:397–402; Ashby et al (1997) *Regul Toxicol Pharmacol* 25:226–31, Long et al, (1998) J Steroid Biochem Mol Biol 67:293–304. In addition, estrogen activity modulators obtained from plants or foods can be used, including soy and soy isoflavones, including genistein and daidzein, as described in Xu et al (1998) *Cancer Epidemiol Biomarkers Prev* 7:1101–8, Charland et al (1998) *Int J Mol Med* 2:225–228, Franke et al (1998) *Am J Clin Nutr* 68:1466S-1473S, Kim et al (1998) *Am J Clin Nutr* 68: 1418S-1425S, Shao et al (1998) *Cancer Res* 58:4851–7, Shao et al, *Journal of Cellular Biochemistry* 69(1):44–54, 1998; Liggins et al (1998) *Anal Biochem* 264:1–7, Kinoshita et al (1998) *Adv Exp Med Biol* 439: 1178–29, and Dees and Kennedy (1998) *Curr Opin Oncol* 10(6):517–522. Estrogen activity modulators that are aromatase inhibitors are described in Mor et al (1998) *J Steroid Biochem Mol Biol* 67(5–6):403–411; Goss et al (1999) *Oncology* 56(2):114–121; Coombes (1998) *Recent Results Cancer Res* 152:277–84; Costa et al (1999) *Cancer* 85:100–3; Long et al (1998) *J Steroid Biochem Mol Biol* 67(4): 293–304; and Lamb and Adkins (1998) *Drugs* 56(6):1125–40. Gonadotropin hormone releasing agonists (GnRHA) are described at website www.amaassn.org/special/womh/newsline/reuters/03315440.htm (date Apr. 5, 1999); and in other publications including Jonat (1998) Br J Cancer 78 Suppl 4:5–8; Szamel et al (1998) *Cancer Chemother Pharmacol* 42(3):241–6; Ciardo et al (1998) *Minerva Ginecol* 50(1–2):25–29; Nagy et al (1996) *Proc Natl Acad Sci USA* 93(14):7269–73; Burger et al (1996) *Eur J Obstet Gynecol Reprod Biol* 67(1):27–33.

The method is practiced by providing a ductal fluid sample from at least one duct of a breast of the patient. Providing the ductal fluid sample can comprise obtaining the sample from the breast. Providing the ductal fluid sample can also comprise receiving a sample which had been previously obtained. For example, a laboratory can receive a ductal fluid sample from a patient or a practitioner, and the laboratory can be directed to make an analysis of the sample. Where the fluid is obtained from the breast, the fluid sample can be obtained e.g. by nipple aspiration of the milk ducts or by ductal lavage of at least one breast milk duct. When fluid is collected by nipple aspiration, or by ductal lavage, the fluid can be collected from a single duct. For example the duct and the collection tube can be marked so that the analysis of the fluid is traceable to one duct.

Accessing the breast duct is considered to be a non-invasive means of retrieving samples of ductal epithelial cells from the breast duct because although the ductal lumen is accessed, but tissue is not ruptured, penetrated, broken or violated. By the procedure of ductal lavage, ductal epithelial cells that line the walls of the ductal lumen are washed out of the duct. Lavage or wash fluid is infused into the duct, and the lavage fluid mixed with ductal fluid is collected. In some cases suction can be applied to the tool accessing the ductal lumen in order to retrieve a maximum amount of cells and/or fluid. Nipple aspiration of breast ductal fluid is achieved by using vacuum pressure. Both lavage and nipple aspiration are considered non-invasive means to collect and/or retrieve ductal fluid and/or ductal epithelial cells.

Nipple aspirate fluid can be retrieved as described in e.g. Goodson W H & King E B, Chapter 4: *Discharges and Secretions of the Nipple*, The Breast: Comprehensive Management of Benign and Malignant Diseases (1998) $2^{nd}$ Ed. vol 2, Bland & Kirby eds. W.B. Saunders Co, Philadelphia, Pa. pp. 51–74; Wrensch et al., (1992) American Journal of Epidemiology. 135(2):130–41; and Sauter et al (1997) British Journal of Cancer. 76(4):494–501. Ductal lavage is described in copending patent application U.S. Ser. No. 09/067,661 filed Apr. $28^{th}$, 1998. Cells of the lesion can be retrieved by collecting the ductal fluid that contains some of these cells, e.g. by aspirating the nipple to obtain nipple aspirate fluid, e.g. as described in Petrakis (1993) *Cancer Epidem. Biomarker Prev.* 2:3–10, Petrakis (1986) *Breast Cancer Res. Treat* 8: 7–19, Wrensch et al (1992) *Am. J Epidem.* 135:130–141, Wrensch et al (1990) *Breast Cancer Res Treat* 15: 39–21, and Wrensch et al (1989) *Cancer Res.* 49: 2168–2174. Also fluid secretions from the nipple can be collected as they spontaneously appear on the nipple surface.

Access of a breast duct can also be facilitated as described in e.g. Love & Barsky, (1996) *Lancet* 348: 997–999, Makita et al (1991) *Breast Cancer Res Treat* 18: 179–188, or Okazaki et al (1991) *Jpn J. Clin. Oncol.* 21:188–193. The principles of access of the duct include that breast tissue is not violated, that the ductal lumen is accessed, but tissue is not ruptured. A medical tool can be placed in the duct and at a contact with the lesion or with fluid in the duct, fluid and/or cells can be retrieved. Alternatively, ductal fluid can be retrieved by a medical tool, e.g. a catheter or a cannula to wash or lavage the duct thereby mixing wash fluid with duct fluid and retrieving the mixture of fluids. The fluid from the breast duct can contain ductal epithelial cells, including cells of a stage considered to be precancerous or cancerous.

The ductal fluid may also be analyzed in situ, i.e. inside the breast, e.g. where a particular marker can be introduced into the duct and can be identified from within the breast. In situ testing within the duct is also considered a non-invasive means of examining the ductal epithelial cells. Ductal epithelial cells that are examined by the method of the invention can be examined in situ (i.e. in the duct; e.g. where a marker can bind the cells or a component of the cells in the duct and be identified from within the breast by a tag attached to the marker), or after the ductal epithelial cells have been removed from the breast of the patient by non-invasive means, e.g. as just described. Methods of in situ analysis can include use of such molecular biology tools, methods, and materials as described in e.g. U.S. Pat. No. 5,169,774, U.S. Pat. No. 5,720,937, U.S. Pat. No. 5,677,171, U.S. Pat. No. 5,720,954, U.S. Pat. No. 5,725,856, U.S. Pat. No. 5,770,195, and U.S. Pat. No. 5,772,997. Markers to breast cancer and breast precancer described elsewhere and herein may also be used for an in situ analysis of the breast duct.

The ductal fluid is then examined to determine the presence of precancerous or cancerous ductal epithelial cells. The fluid sample (including ductal fluid that comprises ductal epithelial cells) can be analyzed by any effective means for identifying breast precancer or cancer. Thus the fluid itself can be analyzed for the presence of soluble factors or other components that might indicate the presence of cancerous or precancerous ductal epithelial cells in the duct. The ductal epithelial cells retrieved in the fluid can be analyzed for protein markers, nucleic acid markers, chromosomal abnormalities, or other characteristic changes that would signal the presence of cancerous or precancerous cells. In addition, other cells found in the fluid can also be analyzed, e.g. for an increase or decrease in these cells as compared to normal ductal fluid, or for qualities of these cells themselves. Thus, the fluid can be analyzed (e.g. for soluble protein content or presence of other ductal fluid components, including also secreted products of ductal epithelial cells) or the ductal epithelial cells themselves can be analyzed, for example, for cell morphology, for protein markers, for nucleic acid markers, and for biochemical markers. In addition, the cells can be analyzed for morphological abnormalities in cell components, including, e.g. morphological abnormalities of the nucleus, cytoplasm, golgi apparatus or other parts of a cell. The cells can be analyzed for whether they do or don't aggregate (e.g. in clumps) or by making comparisons of the ductal epithelial cells with other cell types retrieved in the ductal fluid (e.g. macrophages, lymphocytes, foam cells and other possible components of ductal fluid). Ductal epithelial cells or components of the ductal fluid can be analyzed in situ, in the breast. In situ, in the breast, the ductal epithelial cells can be analyzed for their relationship to other (e.g. neighboring or distant) ductal epithelial cells, to other cells in the lumen or surrounding the lumen, (including e.g. myoepithelial cells), and for the molecular contents or the morphology of the ductal epithelial cells, including, e.g. protein markers, nucleic acid markers, biochemical markers in the cells or on the cell surfaces or for any evidence of neoplasia.

Some exemplary markers are listed below in the section that discusses monitoring patients. Many biological markers are listed in Porter-Jordan and Lippman, "Overview of the biological markers of breast cancer", Hematology/Oncology Clinics of North America vol. 8 (1):73–100, 1994). Some markers that are presently being studied by researchers presently include, carcinoma embryonic antigen (CEA), prostate specific antigen (PSA) Erb B2 antigen, gross cystic disease fluid protein-15 (GCDFP-15), and lactose dehydrogenase (LDH). For CEA see Imayama, Mori et al Cancer 1996, 78(6):1229–34; Inaji, Yayoi et al Cancer 1987,60(12):3008–13; Mori Int Conger Seer 1989, 807:211–8; Inaji, Koyama An To Kagaku Ryoho 1991, 18(2):313–7; Yayoi, Furukawa, et al Gan To Kagaku Ryoho 1994, 21 Suppl 2:133–9; Mori, Inaji, et al Jpn J Clin Oncol 1989,19(4):373–9; Foretova, Verselis, et al Proc Annu Meet Am Soc Clin Oncol 1995,14:A101; and Nishiguchi, Hishimoto et al Rinsho Byori 1992,40(1):67–72. For PSA see Foretova, Garber Lancet 1996,347(9015):1631; Sauter E R. Daly M. Linahan K. Ehya H. Engstrom P F. Bonney G. Ross E A. Yu H. Diamandis E., Prostate-specific antigen levels in nipple aspirate fluid correlate with breast cancer risk, Cancer Epidemiology, Biomarkers & Prevention. 5(12):967–70, 1996 Dec; Sauter and Daly (1996) *Proc Annu Meet Am Assoc Cancer Res* 37: A1458; and Foretova and Garber (1996) *Proc Annu Meet Am Assoc Cancer Res* 37: A1446. For Erb B2 see Motomura (1995) *Breast Cancer Res and Treat* 33:89–92; and Inaji et al (1993) *Tumour Biol* 14: 271–8. For GCDFP-15 see Petrakis et al (1994) *Proc Annu Meet Am Assoc Cancer Res* 35: A1698. For LDH see Mannello et al (1995) *Cancer* 76:152–4; and Kawamoto (1994) *Cancer* 73:1836–41.

Chromosomal abnormalities in ductal epithelial cells can also provide information and act as a marker to identify cancer or precancer as described in Mark et al (1999) *Cancer Genet Cytogenet* 108:26–31; Lundlin and Mertens (1998) *Breast Cancer Res Treat* 51:1–15; Newsham (1998) *Am J Pathol* 153:5–9; Larson et al (1998) *Am J Pathol* 152:1591–8; Adelaide et al (1998) *Genes Chromosomes Cancer* 22:186–99; Fejzo et al (1998) *Gene Chromosome Cancer* 22:105–113; Dietrich et al (1998) *Hum Pathol* 12: 1379–82; Cavalli et al (1997) *Hereditas* 126:261–8; Adeyinka et al (1997) *Cancer Genet Cytogenet* 97:119–21; Afify and Mark (1997) *Cancer Genet Cytogenet* 97:101–5; Brenner and Aldaz (1997) *Prog Clin Biol Res* 396: 63–82; Mark et al (1997) *Ann Clin Lab Sci* 27:47–56; and Fabian et al 1993 *J. Cellular Biochemistry* 17G:153–16.

In addition, exemplary markers are described in Masood S., (Prediction of recurrence for advanced breast cancer. Traditional and contemporary pathologic and molecular markers) *Surgical Oncology Clinics of North America*. 4(4):601–32, 1995; Lopez-Guerrero et al (1999) *J Hematother* 8(1):53–61; Madjumdar and Diamandis (1999) *Br J Cancer* 79(9–10):1594–602; Balleine et al (1999) *Br J Cancer* 79 (9–10):1564–71; Houston et al (1999) *Br J Cancer* 79(7–8):1220–6; Nikolic-Vukosavljevic et al (1998) *Tumori* 84(6):691–4; Maguire et al (1998) *Int J Biol Markers* 13(3):139–44; Stearns et al (1998) *Breast Cancer Res Treat* 52(1–3):239–59; Eiriksdottir et al (1998) *Eur J Cancer* 34(13):2076–81, and U.S. Pat. No. 5,169,774. Many known breast cancer markers are discussed and described in readily available medical text books on breast cancer. In addition, several markers can be identified and analyzed in the same sample, e.g. Fabian et al 1993 *J. Cellular Biochemistry* 17G: 153–16 and Fabian et al 1994 *Breast Cancer Res Treat* 30(3):263–74 looking at estrogen receptor (ER), epidermal growth factor receptor (EGFR), mutant p53, HER-2 neu by immunohistochemistry and aneuploidy by image analysis in fine needle aspirates.

Examination of the ductal epithelial cells can be accomplished by examining useful indicators such as, e.g. the morphology of the cells or cellular contents. The cellular contents can include, e.g. protein, nucleic acid, or other molecular markers in the cells. Cell morphology can serve to establish whether the ductal epithelial cells are normal (i.e. not precancerous or cancerous or having another non-cancerous abnormality), precancerous (i.e. comprising hyperplasia, atypical ductal hyperplasia (ADH) or low grade ductal carcinoma in situ (LG-DCIS)) or cancerous (i.e. comprising high grade ductal carcinoma in situ (HG-DCIS), or invasive carcinoma). Analysis of cell contents may serve to establish similar staging as established by morphology, capturing generally a progression of a precancerous or cancerous condition in the cells.

When examining the cell morphology of ductal epithelial cells retrieved from the ductal fluid of a patient, it is important to note that the appearance and character of ductal epithelial cells retrieved by nipple aspiration of the breast milk ducts or ductal lavage of a breast milk duct is unique. Special consideration and parameters for analysis are established to make the examination of these cells in the context of how they are collected from the patient or provided to the clinical lab making the examination. Presently, to determine the cell morphology of ductal epithelial cells retrieved in ductal fluid, cytology is frequently used. Although many parallels and some analogous learning can be adopted from methods of analyzing cells that are retrieved by fine needle aspiration (FNA) of lesions in breast cancer by cytology or histology, (or other biopsy materials retrieved from the breast) the process of examination of ductal epithelial cells retrieved by nipple aspiration or lavage is distinct from an analysis made by FNA or biopsy. Cells retrieved by nipple aspiration or lavage are ductal epithelial cells released into the ductal lumen or washed into the ductal lumen. These cells have not been mixed with disrupted cells in the breast tissue that surrounds the lumen. Often the ductal epithelial cells are retrieved in clumps of other ductal epithelial cells, in which case the morphological character of the clump can also be noted. Cells retrieved by FNA or biopsy are mixed with breast tissue cells, and other components of disrupted breast tissue including blood. The breast tissue is disrupted by the needle or knife that enters the tissue, and this disruption is reflected in the analysis of an FNA or other biopsy sample. In addition, the physical disruption of the tissue risks exacerbation of any precancerous or cancerous condition in the breast duct by breaking tissue and risking unclean margins. Ductal epithelial cells retrieved in ductal fluid from the lumen of a breast milk duct, on the other hand are in contact only with other ductal epithelial cells, and with other contents of the ductal fluid. As such a sample of ductal epithelial cells retrieved by nipple aspiration or ductal lavage is very close to its native context, and analysis made on these cells, whether by morphology, cytology, analysis of cellular contents or analysis of another marker or another indicia of cell stage progression in precancer or cancer provides the opportunity for a sensitive and accurate analysis of the condition of the breast duct from which the cells are retrieved, and provides the opportunity to analyze the condition of the breast duct without risking exacerbation of any precancer or cancer existing in the breast duct.

Cytological assays that can be performed on the cells retrieved from a duct or from nipple aspirate can include e.g. assays described in King et al, *J. Nat'l Cancer Inst* (1983) 71:1115–21, Wrensch et al. (1992) *Am. J Epidem*. 135: 130–141, Papanicolaou et al, (1958) *Cancer*, 11:377–409 and Goodson W H & King E B, Chapter 4: *Discharges and Secretions of the Nipple*, THE BREAST: COMPREHENSIVE MANAGEMENT OF BENIGN AND MALIGNANT DISEASES (1998) $2^{nd}$ Ed. vol 2, Bland & Kirby eds. W.B. Saunders Co, Philadelphia, Pa. pp. 51–74. For example, as described in Goodson and King (page 60) atypical hyperplasia presents having cellular abnormalities, increased coarseness of the chromatin and tendency for more single cells as well as groups of cells. With regard to carcinoma in situ, Papanicolaou et al, described cellular abnormalities, e.g. nuclear abnormalities diagnosed by cytology of fluid from nipple secretions containing ductal cells. The cytology of abnormal cells can also be conducted as described in Sartorius et al (1977) *J. Natl Cancer Inst* 59: 1073–1080. and King et al, (1983) JNCI 71(6) 1115–1121. Atypia and carcinoma in situ are widely characterized pathologically, as described in Page et al, (1998) *Mod Pathol* 11(2): 120–8. The ductal fluid can be analyzed by cytological techniques by placing some of the fluid on a slide with a standard cytological stain using a light microscope. The cells can be studied for atypical growth patterns in individual cells and clusters of cells using published methods, including Mouriquand J, (1993) S Karger Pub, "Diagnosis of Non-Palpable Breast Lesions: Ultrasonographically Controlled Fine- Needle Aspiration: Diagnostic and Prognostic Implications of Cytology" (ISBN 3805557477); Kline T S and I K, Pub Igaku-Shoin Medical" "Breast: Guides to Clinical Aspiration Biopsy" (LSBN 0896401596; Masood, *American Society of Clinical Pathology*: Nov. 199S, "Cytopathology of the Breast" ISBN 0891893806; and Feldman PS, *American Society of Clinical Pathology*, Nov. 1984, "Fine Needle Aspiration Cytology and Its Clinical Applications: Breast and Lung" ISBN 0891891846.

Other references that discuss cytological analysis and which give guidance to an analysis of ductal epithelial cells derived from ductal fluid include Silverman et al, (Can FNA biopsy separate atypical hyperplasia, carcinoma in situ, and invasive carcinoma of the breast?: Cytomorphologic criteria and limitations in diagnosis, Diagnostic Cytopathology. 9(6):713–28, 1993; Masood et al, (Immunohistochemical differentiation of atypical hyperplasia vs. carcinoma in situ of the breast.) Cancer Detection & Prevention. 16(4):225–35, 1992; Masood et al, (Cytologic differentiation between proliferative and nonproliferative breast disease in mammographically guided fine-needle aspirates) *Diagnostic Cytopathology*.7(6):581–90, 1991; Masood S. (Occult breast lesions and aspiration biopsy: a new challenge) Diagnostic Cytopathology. 9(6):613–4, 1993; Masood S., (Prognostic factors in breast cancer: use of cytologic preparations) *Diagnostic Cytopathology*. 13(5):388–95, 1995; Novak and Masood, (Nuclear grooves in fine-needle aspiration biopsies of breast lesions: do they have any significance?) *Diagnostic Cytopathology*. 18(5):333–7, 1998; Sidawy et al, (Interobserver variability in the classification of proliferative breast lesions by fine-needle aspiration: results of the Papanicolaou Society of Cytopathology Study) *Diagnostic Cytopathology*. 18(2):150–65, 1998; Masood et al, (Automation in cytology: a survey conducted by the New Technology Task Force, Papanicolaou Society of Cytopathology) *Diagnostic Cytopathology*. 18(1):47–55, 1998; and Frykberg and Masood Copeland EM 3d. Bland KI., (Ductal carcinoma in situ of the breast) *Surgery, Gynecology & Obstetrics* 177(4):425–40, 1993.

Another example of ways to examine the ductal epithelial cells retrieved from a patient's breast duct fluid is to detect the presence of estrogen receptor in these cells. See also Sukumar et al, (Independent molecular pathways in initiation and loss of hormone responsiveness of breast carcinomas) Science, 240(4851):524–6, 1988 for a discussion of the relevance and usefulness of identifying hormone responsiveness in breast cancer. The presence of estrogen receptor can be tested by any standard technique available for detecting the presence of proteins generally in cells. In precancer and some early cancer, it is expected that the estrogen receptor will be positive (i.e. 20% or greater staining by a standard estrogen receptor test). In later cancers and some early cancers, the estrogen receptor may be negative (i.e. less than 20% staining or less in the cells analyzed). In general a reduction in staining percentage in a cell population (e.g. a sample on a slide) indicates that the patient condition is worsening, i.e. that the precancer or cancer is progressing to a worse cell stage. Detection of the estrogen receptor in ductal epithelial cells for identifying asymptomatic patients who are likely to benefit from the administration of an estrogen activity modulator can depend on the particular assay used to detect the estrogen receptor. Some assays provide methods to quantify the results of the tests. Normal cells of the ductal epithelium can be expected to have a high base line of estrogen receptor, i.e. all normal ductal epithelial cells can be expected to stain or register positive for estrogen receptor. Cells that become progressively cancerous, moving from normal to precancerous to cancerous can be expected at some point in that continium to have more and more ductal epithelial cells that do not have estrogen receptor. However, even a sample from ductal epithelium having malignant cells may be expected to have some estrogen receptor present in some cells. Thus, detection of estrogen receptor can be measure against a control, e.g. normal cells, in order to draw conclusions about the state of the estrogen receptor for the cell sample of interest.

Assays for testing for the presence of ER can include standard cytoplasmic protein and/or receptor detection assays provided by standard protocol books, e.g. in Sambrook, 1989, *Molecular Cloning, A Laboratory Manual*, 2d Ed., Cold Spring Harbor Laboratory Press, Cold Spring Harbor, N.Y., and Ausubel et al., *Current Protocols in Molecular Biology*, 1987–1997 Current Protocols, 1994–1997 John Wiley and Sons, Inc.). Assays to test for ER presence can also be conducted, e.g. as described in Jacobs et al, (1996) *Eur J Cancer* 32A:2348–53, Pertschuk et al, (1996) *Gynecol Oncol* 63:28–33, Molino et al, (1995) *Breast Cancer Res Treat* 34:221–8, Esteban et al, (1994) *Am J Clin Pathol* 102:158–62, Pertschuk et al, (1994) *J Cell Biochem Suppl* 19:134–7, Poller et al, (1993) *Br. J Cancer* 68:156–61, Chapman et al, (1993) *J Steroid Biochem Mol Biol* 45:367–73, Davies et al, (1991) *Ann R Coll Surg Engl* 73:361–3, Sklarew et al, (1990) *Cytometry* 359–78, Mobus et al, (1998) *Int J Cancer* (1998) 77(3): 415–23, Mohamood et al, (1997) *J Submicrosc Cytol Pathol* 29(1):1–17, and Jensen, EV, (1996) *Ann NY Acad Sci* 784:1–17. For example, estrogen receptor immunocytochemistry ER-ICA (available from Abbott laboratories, located in Abbott Park, Ill.) can be used to identify and quantify the ER from a sample of breast milk duct fluid in order to establish an ER positive condition of ductal epithelial cells retrieved from the milk duct. The ER-ICA test has been used in FNA procedures to identify estrogen receptors as describe in Azavedo et al, (1986) *Anticancer Research* 6:263–266; Fabian et al (1997) *J Cell Biochem Suppl* 28–29: 101–110; Flowers et al (1986) *Ann. Surg.* 203:250–254; McClelland et al, (1987) *Cancer Research* 47: 6118–6122; Sauer et al (1998) *Anal Quant Cytol Histol* 20(2): 122–126; Tabbara et al (1998) *Cancer* 84(6): 355–360. Other analysis using estrogen receptors include those described in Masood and Johnson (The value of imprint cytology in cytochemical detection of steroid hormone receptors in breast cancer) *American Journal of Clinical Pathology* 87(1):30–6, 1987; Barnes and Masood (Potential value of hormone receptor assay in carcinoma in situ of breast) *American Journal of Clinical Pathology*. 94(5):533–7, 1990; Masood S., (Fluorescent cytochemical detection of estrogen and progesterone receptors in breast fine-needle aspirates) *American Journal of Clinical Pathology*. 95(1):35–40, 1991; Masood S., (Use of monoclonal antibody for assessment of estrogen and progesterone receptors in malignant effusions) *Diagnostic Cytopathology*. 8(2):161–6, 1992; Masood S., (Use of monoclonal antibody for assessment of estrogen receptor content in fine-needle aspiration biopsy specimen from patients with breast cancer) *Archives of Pathology & Laboratory Medicine*. 113(1):26–30, 1989; Johnson et al (Prognostic factors in node-negative breast cancer) *Archives of Surgery*. 127(12):1386–91, 1992; Masood S., (Immunocytochemical localization of estrogen and progesterone receptors in imprint preparations of breast carcinomas) *Cancer*. 70(8):2109–14, 1992; Masood S., (Prognostic and diagnostic implications of estrogen and progesterone receptor assays in cytology) *Diagnostic Cytopathology* 10(3):263–7, 1994; Masood S., (Estrogen and progesterone receptors in cytology: a comprehensive review) *Diagnostic Cytopathology.* 8(5):475–91, 1992; Gilbert et al., (A pilot study of pi-class glutathione S-transferase expression in breast cancer: correlation with estrogen receptor expression and prognosis in node-negative breast cancer) *Journal of Clinical Oncology.* 11(1):49–58, 1993; Masood et al, (Potential value of estrogen receptor immunocytochemical assay in formalin-fixed breast tumors) *Modern Pathology.* 3(6):724–8, 1990; Masood et al, (Application of estrogen receptor immunocytochemical assay to aspirates from mammographically guided fine needle biopsy of nonpalpable breast lesions) *Southern Medical Journal.* 84(7):857–61, 1991.

Another way to examine the ductal epithelial cells retrieved from a patient's breast duct fluid is to detect the presence of TGF-β in the ductal fluid. The ductal fluid and/or ductal epithelial cells contained in that fluid can be analyzed for the presence of transforming growth factor-beta (TGF-β). The presence or amount of TGF-β in a fluid or sample is measure against a control, e.g. the presence or amount of TGF-β in a normal sample. It is expected that normal fluid or cells will demonstrate a certain baseline quantity of TGF-β from which a test sample can be measure. Thus, detecting TGF-β to identify asymptomatic patients who are likely to benefit from administration of an estrogen activity modulator requires detecting a level of TGF-β above the baseline normal level, whatever that is determined to be. Normal can be determined from a patient or a population. The absence of TGF-β means that TGF-β is not expressed or present in quantities greater than the quantities expressed or present for normal individuals. The presence of significant levels of TGF-β can indicate that the cancer may be developing resistance to an estrogen activity modulator. Also, when TGF-β is detected and/or increases from a previously measured level the cancer or precancer may be progressing to a worse cell stage. TGF-β levels can be tested in the fluid and/or cells derived from the breast duct, including use of standard tests for the presence of soluble proteins, or cellular proteins (including cell surface forms), e.g. tests using labeled antibodies to TGF-β.

Standard ELISA tests (e.g. ELISA tests available from companies providing assays and reagents for molecular biology, e.g. Promega Corporation, located in Madison, Wis.) for TGF-β can be used. Another exemplary means of testing for TGF-β can be polymerase chain reaction (PCR) protocols to test levels of TGF-β mRNA encoding the protein, or other appropriate standard tests for testing protein or transcript levels can also be used. Standard detection assays for proteins or RNA transcripts of genes such as TGF-β are provided by standard protocol books, e.g. in Sambrook, 1989, *Molecular Cloning, A Laboratory Manual*, 2d Ed., Cold Spring Harbor Laboratory Press, Cold Spring Harbor, N.Y., and Ausubel et al., *Current Protocols in Molecular Biology*, 1987–1997 Current Protocols, 1994–1997 John Wiley and Sons, Inc. In addition, TGF-β can be tested as described in Li et al, (1998) *J Immunol Methods* 218:85–93 (either bound or unbound from its receptor), Li et al, (1998) *Int J Cancer* 79:455–459, Plath et al (1997) *J Endocrinol* 155:501–11, Amoils et al (1996) *Br J Cancer* 73:1255–9, Walker and Gallacher (1995) *J Pathol* 177:123–7, Danielpour and Roberts (1995) *J Immunol Methods* 180:265–71, and Gall et al (1993) *J Clin Pathol* 46:378–9, Walker and Dearing (1992) *Eur J Cancer* 28: 641–4, and Relf et al (1997) *Cancer Res* 57:963–9. Additional markers include others discussed, described and cited herein, including e.g. such markers as carcinoma embryonic antigen (CEA), prostate specific antigen (PSA), Erb B2 antigen, gross cystic disease fluid protein-15 (GCDFP-15), or lactose dehydrogenase (LDH) in the ductal fluid. Chromosomal abnormality in the ductal epithelial cells can also be used as a marker of precancer or cancer.

Patients determined to have precancerous or cancerous ductal epithelial cells are likely to benefit from administration of an estrogen activity modulator. See e.g. el Khissiin and Leclercq, (1998) *Steroids* 63(11): 565–74; O'Regan et al (1998) *J Nat'l Cancer Inst* 90(20):1552–8; Favoni and Cupis (1998) *Trends Pharmacol Sci* 19(10): 406–15; Williams, G M (1998) *J Nat'l Cancer Inst* 90:1671; Huynh et al (1996) *Clin Cancer Res* 2:2037–2042; England and Jordan (1997) *Oncol Res* 9:397–402; Ashby et al (1997) *Regul Toxicol Pharmacol* 25:226–31, Long et al, (1998) J Steroid Biochem Mol Biol 67:293–304 for studies indicating a likely benefit from administration of these estrogen activity modulators for the treatment of breast cancer. See, e.g. Fisher et al, (1998) *J Nat'l Cancer Inst*, vol. 90 (18): 1371–1388 for evidence that administration of tamoxifen to patients having breast precancer is of benefit to reduce the risk of getting breast cancer.

Appropriate animal models for breast cancer therapies have been described, e.g. McKenzie and Sukumar, (Molecular mechanisms of chemical carcinogenesis in rodent models) *Cancer Treatment & Research* 71:313–29, 1994; Chen et al, (Midkine in the progression of rat N-nitroso-N-methylurea-induced mammary tumors) *Molecular Carcinogenesis.* 17(3): 112–6, 1996; and Sukumar et al, (Animal models for breast cancer) *Mutation Research* 333(1–2):37–44, 1995.

The patient population that is identified by the method of the invention as having either or both precancerous or cancerous ductal epithelial cells is considered most likely to benefit from administration of an estrogen activity modulator. Any precancer is identifiable. Any cancer is identified earlier than by standard cancer tests. No tissue is broken or disrupted. Detection of cancer is more sensitive than standard cancer tests. Thus the invention presents a considerable advancement over the prior art by providing a more sensitive, accurate, and patient-friendly method of examination and identification of a certain patient population, a patient population that is ripe for a particular treatment. The invention provides the opportunity to identify a patient population when they are most likely to benefit from administration of estrogen activity modulators. If given at an optimal time in the progression of a patient's precancer or cancer, estrogen activity modulators stand the greatest chance for success in reducing a patient's risk of getting breast cancer, or dying from it. Previously this patient population has gone unidentified (and thus untreated) for either breast precancer or early stage breast cancer. The method is also able to identify cancer in more advanced stages, with the advantage that the cancer is not disrupted by the identification and therefore the cancer is not exacerbated due to tissue cutting or unclean margins.

Thus, the invention provides a method of risk reduction or therapeutic treatment of an asymptomatic patient at risk for developing breast cancer by administering an estrogen activity modulator to a patient having precancerous or cancerous ductal epithelial cells in a duct of a breast of the patient. The determination of the presence of precancerous or cancerous ductal epithelial cells can be made from analysis of fluid comprising ductal epithelial cells that is collected from the milk duct of a breast of the patient, as described above. The fluid can be collected by nipple aspiration of the milk ducts or by ductal lavage of at least one breast milk duct. The fluid can be collected from a single duct. Whether precancerous or cancerous ductal epithelial cells are present can be determined by any appropriate analysis of the cells or fluid, as described above, including, e.g. cytological analysis of the ductal epithelial cells also as described above. The analysis can further comprise, e.g., detecting the presence of estrogen receptor in the ductal epithelial cells or detecting the absence of TGF-β in the ductal fluid or cells as described above.

The estrogen activity modulator to be administered can be any estrogen activity modulator. As such, the estrogen activity modulator can comprise a class of agents including a selective estrogen receptor modulator (SERM), an estrogen antagonist, an estrogen antagonist, or a modulator of estrogen synthesis. The estrogen activity modulator can be tamoxifen, raloxifene, EM 800, droloxifene, ioxdroxifene, RU 39411, RU 58668, ICI 164384, faslodex, soy, a soy isoflavone, a gonadotropin releasing hormone agonist, or an aromatase inhibitor. The soy isoflavone can be genistein or daidzein. The aromatase inhibitor can be toremifene.

The estrogen activity modulator may be administered by systemic or local means. Systemic administration can include oral or parenteral administration. The parenteral administration can include, e.g. intravenous, intramuscular administration, intramucosal administration (e.g. intranasal or intrabronchial administration) or injection into tissue, or by any other means of parenteral administration. Systemic administration can also include any other means which comprises a systemic distribution of the estrogen activity modulator to the patient.

The estrogen activity modulator can be administered locally, including an injection into breast tissue, or intraductal administration. The intraductal administration can comprise accessing the breast duct and administering the estrogen activity modulator, e.g. by accessing the breast duct using a cannula or catheter. The agent can be delivered in a liquid form, a gel form, or a capsule or plug to the duct. Thus, the intraductal administration can comprise a mode selected from the group consisting of catheterization of a liquid or gel, cannulation of a liquid or gel, use of a pump to infuse agent into a duct or ducts, and introduction of a time-release capsule into a duct. The time-release capsule can be placed in the lactiferous sinus of a breast milk duct. The capsule can be biodegradable and/or a time release capsule. The time-release capsule can be formulated using an estrogen activity modulator as the active agent essentially as described in U.S. Pat. No. 5,676,972 or U.S. Pat. No. 5,613,059. The time release capsule so formulated and administered intraductally, may also contain agents other than a estrogen activity modulator for an appropriate therapeutic purpose for treatment precancer or cancer in a duct.

As an alternate intraductal administration, a small pump may be installed in the duct or at the surface of the nipple with access to the duct for slow continuous administration of the estrogen activity modulator to the ductal region, e.g. a pump may be installed in the lactiferous sinus for administering the agent therein and causing a diffusion of the agent to the rest of the duct or the pump may be installed on the nipple surface with access to the duct. A pump installed at the nipple surface can be shaped e.g. like a tack (or a thimble-shaped portion having a top or tack portion) and rest on the nipple surface with a portion extending into a duct requiring treatment. The pump mechanism can comprise e.g. a Duros™ osmotic pump, manufactured by Alza Corporation located in Palo Alto, Calif. The pump mechanism for intraductal administration can reside in the tack-head portion of the pump resting on the nipple surface. Below the tack-head of the pump can extend a tip portion that is placed into a duct so that the pump delivers its agent into the tip and thus into the duct. The osmotic pump may also be assembled or configured essentially as the pumps described in U.S. Pat. No. 5,531,736, U.S. Pat. No. 5,279,608, U.S. Pat. No. 5,562,654, U.S. Pat. No. 5,827,538, U.S. Pat. No. 5,798,119, U.S. Pat. No. 5,795,591, U.S. Pat. No. 4,552,561, or U.S. Pat. No. 5,492,534, with appropriate modifications in size and volume for administration to the duct of a breast, e.g. for placement into the duct (e.g. the lactiferous sinus) or for placement on the nipple surface. The tip (that accesses the duct) may be able to rotate in order to accommodate ducts of various positions on the nipple surface. A single tack-head pump can have one or more tips placed below the tack-head in order to access a particular duct or ducts, e.g. where two or more ducts in a breast need to be accessed. The pump so configured and loaded with an appropriately formulated agent for intraductal administration, may administer a estrogen activity modulator as described, but may also contain and administer agents other than a estrogen activity modulator for an appropriate therapeutic purpose for treatment of a precancer or cancer condition in a breast duct. Conceivably the pump may be configured to administer to all the ducts located in the breast, with some size and volume alterations.

Other alternative intraductal delivery of estrogen activity modulators can include a delivery system described in U.S. Pat. No. 5,840,059 adapted appropriately for intraductal delivery to a breast milk duct, and that described in U.S. Pat. No. 4,711,251 also appropriately adapted for intraductal delivery to breast milk duct. These alternative intraductal modes may provide for SERM administration, and may also provide for delivery of other agents appropriately formulated for an appropriate therapeutic purpose for of a precancer or cancer condition in a breast duct.

Another alternative intraductal administration can comprise placing small hollow tubes in the openings of the duct and using these semi-permanent tubes having a port opening as access units for accessing the duct on a routine basis (e.g. with a needle, cannula or catheter) for administration of a liquid or gel formulation (containing an estrogen activity modulator) to the duct. Intraductal administration can be accomplished by e.g. needle, catheter or cannula capable of accessing the duct and delivering an estrogen activity modulator-containing agent to the duct where it can affect the lesion. A delivery to a specific duct is particularly advantageous where all the ducts have been screened for a cancerous or precancerous lesion and a particular duct or ducts has been identified as containing such a lesion. In that situation, local intraductal administration can be effected to the duct or ducts containing lesions, and the other ducts (having benign cytology) are left untreated. The alternative intraductal mode including a hollow tube placed in the duct for easy regular access may provide for estrogen activity modulator administration, and may also provide for delivery of other agents appropriately formulated for an appropriate therapeutic purpose for a precancer or cancer condition in a breast duct. The agent can be delivered the duct generally, or more specifically to the lactiferous sinus of the duct.

The local administration can be topical administration, i.e. where the estrogen activity modulator is applied as a gel or cream to the nipple surface where the estrogen activity modulator can be absorbed into the ducts of the breast from the nipple surface. Preferably before the gel is applied to the nipple surface, a dekeratinizing agent, e.g. a dilute acetic acid, or other dekeratinizing agent, can be applied to the nipple surface, followed by the cream comprising the estrogen activity modulator. The estrogen activity modulator for local delivery can be formulated in a liquid form, a gel, a cream, a liposome formulation, a polymer, a time-release formnulation, a solid, and any other formulation appropriate for the particular local delivery, including e.g. injection into the breast tissue and intraductal delivery. The liposome formulation can comprise liposomes such as described e.g. in WO 96/14864, WO 9713873.1, U.S. Pat. No. 5,512,294, U.S. Pat. No. 5,527,528, EP 36,277, WO 83/02069, U.S. Pat. No. 5,077,057.

Administering an effective dose of the agent comprises taking into account such indicia of disease progression as the cell stage, the size of the lesion, and relative health of the patient, the amount of ER in the cells or in a sample (with less estrogen receptors indicating a need for a stronger dose), and the amount of TGF-$\beta$ in ductal fluid or cells. Other markers may be considered in determining a dosage, including e.g. cell morphology, nucleic acid quantity or quality, nucleic acid markers, protein markers, and other biochemical markers. The dosage of the estrogen activity modulator will also be based on whether the estrogen activity modulator is administered locally or systemically. A local dosage can be extrapolated from a systemic dose by a comparison with analogous conversions of other medicines and agents administered both locally and systemically, e.g. administration of other hormones in other contexts that can be analogized to the estrogen activity modulator administration. The estrogen activity modulator dosage can be determined based on an evaluation of the potency of the particular estrogen activity modulator, and standard dosages for each estrogen activity modulator can be used. The dosage regime for a particular estrogen activity modulator for a particular patient can comprise a regime e.g. such as a single administration, hourly administration, daily administration, weekly administration, administration two times a day, administration two times a week, administration 3 times a week, or administration monthly.

For example, in the case where the estrogen activity modulator tamoxifen is administered systemically, the commercially available formulation sold by Zeneca Pharmaceuticals trademarked Nolvadex can be used at a dosage recommended by the manufacturer and the treating physician, e.g. a range of 10 mg to 40 mg of tamoxifen daily, optimally about 20 mg daily. An appropriate local dosage for the same drug, e.g. delivered intraductally, including as a liquid, capsule, gel, or other formulation might be an appropriate fraction of the systemic dosage, e.g. a range from $\frac{1}{2}$ to $\frac{1}{50}^{th}$ of the systemic tamoxifen daily dosage. Thus, a reasonable range of local dosage might be from 0.2 mg to 20 mg of tamoxifen, at the high end, and from 0.5 mg to 2 mg of tamoxifen at a middle level dosage and at a range from 0.01 mg to 1 mg of tamoxifen at a possible lower end of the extrapolated scale. Where the local administration is not daily, but is e.g. a time release capsule, or weekly catheterization, the daily systemic dosage may be used as a benchmark for extrapolating a daily fraction to be multiplied by 7 (for 7 days in a week) or some other appropriate multiplier depending on the time-release period or the periodicity of the local administration. Thus, for example, a time release capsule having a delivery rate of about 0.2 mg daily to a duct, and a duration of 10 days, may be used. A weekly catheterization protocol may administer 20 mg in a time release gel that is then dispersed into the duct at a rate of about 3 mg per day. It is generally assumed in the calculation of a local dosage from a known advised systemic dosage that the local dosage can be less than the systemic dosage and will still have the same if not better effect in a breast milk duct. It is assumed the these local calculations are provided for on a per lesion basis, and apply to each duct having a lesion and requiring treatment. Thus, for example, the local dosage is doubled where lesions are located in two ducts, and, e.g. a time release capsule is administered to each duct having a lesion.

Comparative actions and assays for testing relative potency and effectiveness of various estrogen activity modulators especially with relation to estrogen receptor activity and other molecular events are described in Lu et al. (1998) *Breast Cancer Res Treat* 50:63–71, Jeng et al. (1998) *Endocrinology* 139:4164–74, Kurebayashi et al. (1998) *Oncology S* 1:23–34, Celius et al. (1999) *Environ Health Perspect* 107:63–68, for purposes including determining relative dosages both for various estrogen activity modulator and for administration of a particular estrogen activity modulator extrapolated from systemic to local dosages.

The invention is also a method for identifying patients who have a decreased likelihood of benefiting from the administration of an estrogen activity modulator for risk reduction or therapeutic treatment of breast cancer comprising providing a ductal fluid sample from a breast of the patient, and examining the ductal fluid sample to determine the presence of transforming growth factor-$\beta$ (TGF-$\beta$), or the absence of estrogen receptor. The presence of TGF-$\beta$ or the absence of estrogen receptor in the ductal fluid sample indicates that the patient is less likely to benefit from the administration of an estrogen activity modulator. Providing the ductal fluid sample can comprise receiving a sample which had been previously obtained (e.g. a patient or practitioner can provide a sample to a laboratory for analysis). The fluid can be obtained by nipple aspiration of the milk ducts or by ductal lavage of at least one breast milk duct. The patients can be receiving an ongoing therapy for risk reduction or treatment of breast cancer. The therapy can comprise administration of an estrogen activity modulator. The patient can have been found to have precancer or cancer of the breast (e.g. by the analysis methods including looking at cell morphology and other markers as described above). The precancer or cancer can be determined by examining a ductal fluid sample of the breast of the patient. The patient can have a family history of breast cancer.

The invention provides also a method for analyzing ductal fluid by providing a ductal fluid sample from a breast of the patient. The method begins with providing the ductal fluid sample from a breast of the patient. The sample can be in the breast of the patient and therefore tested in situ. The sample can be provided to a laboratory or other facility for analysis (e.g. provided by the patient and/or practitioner). The sample can be retrieved from the patient by nipple aspiration (e.g. as described herein). The sample can be retrieved from the patient by ductal lavage (e.g. as described herein). The sample can be obtained from a single breast milk duct of the patient. The sample can also be obtained from more than one breast milk duct of the patient, but the samples can be kept separate to provide the opportunity analyze each duct separately.

The ductal fluid sample, however, obtained, or wherever analyzed (e.g. in the breast, in a laboratory, in a practitioner's office) can be examined to identify a level or quality of at least one marker. A level of the marker can be a presence relative to a normal control or an absence relative to a normal control of a given marker. The normal control can be determined relative to the particular patient, or relative to a patient population. A quality of a marker can be such changes as DNA mutation, or a quantity of mutations, a deterioration of chromosomal quality or quantity, or a change in quantity of a nucleic acid or chromosome. A quality can be an erosion of a molecule or organelle with respect to a normal quality. The marker can be nucleic acid, protein, or biochemical marker.

Thus, the ductal fluid can be examined to identify a level or quality of a marker including transforming growth factor-β (TGF-β), estrogen receptor or chromosomal abnormality. Further, the ductal fluid sample can be examined to identify a level or quality of a second marker. The second marker can include e.g. such markers as carcinoma embryonic antigen (CEA), prostate specific antigen (PSA), Erb B2 antigen, gross cystic disease fluid protein-15 (GCDFP-15), lactose dehydrogenase (LDH), epidermal growth factor receptor (EGFR), or p53. Further, examining the ductal fluid can further comprise cytological examination of the ductal epithelial cells in the sample. Such cytological analysis or analysis of other markers can be conducted for example as described herein.

The invention is also a method of monitoring on-going therapy in a patient at risk of or suffering from breast cancer comprising comparing a first level of a marker measured in a ductal fluid sample taken at a first time with a second level of the marker measured in a ductal fluid sample taken at a later time. The ductal fluid samples can be retrieved from the patient by nipple aspiration or ductal lavage of at least one breast milk duct. The therapy can comprise administration of an estrogen activity modulator. The therapy can also comprise administration of any other drug or treatment of a patient by any other therapy. Where a patient receives a lumpectomy or mastectomy as part or all of the treatment, the patient's remaining ducts and/or breast can be monitored for cancer recurrence. The estrogen activity modulator can comprise a drug in class including a selective estrogen receptor modulator (SERM), an estrogen antagonist, or an inhibitor of estrogen synthesis. The therapy can be begun before the marker is measured. The therapy can be begun after the marker is measured. The marker can be measured periodically.

The marker can be any marker capable of providing a practitioner with information as to the state of the ductal epithelium, a precancerous or cancerous cell stage of the ductal epithelial cells, or a progression or regression of a precancerous or cancerous state in a breast duct in a patient. For example, cell morphology can be studied, the morphology of the cell compartments can be studied, a quantity or presence of a particular nucleic acid, protein or biochemical marker can be identified and/or studied, or a relationship of cells in a context with other cells can also be studied. Chromatin or chromosome character can be studied or identified. The presence or absence of a mutation in a gene can be studied or identified. A combination of such markers can be used to create an index that can be identified and monitored over time. Some markers can include, e.g. presence of neoplastic ductal epithelial cells, appearance or increase of transforming growth factor-β (TGF-β), or reduction of estrogen receptor. Where the marker is neoplastic ductal epithelial cells, the cells can be at a stage selected from the group consisting of hyperplasia, atypical ductal hyperplasia (ADH), low grade ductal carcinoma in situ (LG-DCIS), high grade ductal carcinoma in situ (HG-DCIS) or invasive carcinoma.

In addition to some markers discussed and/or articles or books cited on breast cancer and breast precancer markers, the following cancer markers are listed here as exemplary and may be used as well as other markers to analyze the condition of a breast duct. Standard assay procedures for identifying the markers can be used, including antibodies or other binding partners, labels, stains, pattern analysis (for cells and cell components), and in general any other chemical or visual identification techniques. The following are exemplary potential markers for such identification and analysis:

cathepsins (including cathepsin D)

maspin, fas, fas ligand, tissue inhibitor of matrix metalloproteinas-1 (TIMP-1)

chemokines (both C-C and C-X-C type chemokines)

collagenases, metalloproteinases, TIMP's, cathepsins, disrupted basement membrane epitopes, stromolysin-3 cytokeratins (e.g. keratin 14, B1, KA1, KA4 and 312C8-1)

estrogen and progesterone receptors (or any androgen or other steroid receptor)

growth factor receptors for members of the fibroblast growth family (FGF) including FGF1-18, vascular endothelial growth factor (VEGF), insulin-like growth factor-1 (IGF-I), IGF-II, platelet-derived growth factor (PDGF), keratinocyte growth factor (KGF), and epithelial growth factor (EGF), placental growth factor (PLGF), hepatocyte growth factor (HGF), tumor necrosis factor (TNF), transforming growth factor (TGF) both alpha and beta forms, and angiopoietin, for example growth factors and cytokines including FGF1-18, VEGF, IGF-I, IGF-II, PDGF, KGF, EGF, PLGF, HGF, TNF, TGF alpha and beta, angiopoietin, for example heat shock proteins (HSP) (e.g. HSP27) 27 (HSP27)

ErB type 1 tyrosine kinase receptors (e.g. Her2 (an EGF receptor) or any ligand or receptor of the ErbB family of ligands and receptors)

integrins, selectins, cadherins, for example (i.e. alpha and beta 3 integrin)

keratin-14 known cancer antigens including, for example Ki-67, Ki-S1, p53, nm23, bcl-2, p21 ras, cyclins, and pS2

Thrombin receptor activating peptide urokinase, urokinase-type plasminogen activator (UPA), plasmin antiplasmin, UPA receptor (UPAR), fibrinogen, plasmin activator inhibitor-1 and 2 (PAI-1 and 2)

telomerase antibodies to tumor associated antigen-72 (TAG-72) (e.g. B72.3, B6.2, and TKH2)

carcinoembryonic antigen (CEA) (see e.g. EP 319,686)

prostate specific antigen (PSA)

gross cystic disease fluid protein-15 (GCDFP-15)

lactose dehydrogenase (LDH)

chromosomal abnormalities (e.g. aneuploidy or other abnormalities)

S1 protein alkaline phosphatase myosin sialyl Tn (STn) glycopeptide (e.g. TAG-72)

Tn glycopeptide

In the monitoring process, comparing can comprise determining a change in a marker. The change in a marker can include change in a cellular stage (e.g. progression or regression from one neoplastic cell stage to another), an increase in quantity of a marker, or a decrease in quantity of a marker. A marker may change also by changing form, e.g. where a particular protein truncation is produced and secreted rather than a larger form of the protein. Where morphology in a cell or cell compartment changes, a shape may become less like a normal cell and more like a cancerous cell, i.e. a shape may become more misshapen, smaller, larger, and/or less or more connected to surrounding cells or cell compartments. A marker may be discussed in terms of a level of marker, e.g. where quantity of marker is considered. A level of marker may also be an indication of a cell stage, e.g. a stage such as hyperplasia or high grade ductal carcinoma in situ, where a low level would be hyperplasia and a high level would be ductal carcinoma.

Comparing a first marker level and a later marker level can determine whether the patient is better, worse or unchanged. For example, where the marker is for all practical purposes unchanged in quality, quantity or other indicia, the patient is unchanged. A patient receiving treatment who remains unchanged may be benefiting from the treatment in that the cancer or precancer is being held at bay. However, the general goal of a treatment is to make the patient improve. A patient may be considered to be getting better where a cell stage has regressed to a lesser stage of cancer, or to a precancer from cancer, or to a lesser stage of precancer (e.g. from ductal carcinoma in situ to atypical ductal hyperplasia), or to normal cells. A patient may be considered to be getting worse where a cell stage has progressed to a worse stage of precancer or cancer, where a marker quantity has noticeably increased or decreased (depending on the marker), or a quality of the marker has decreased, e.g. the contents or a particular cell organelle or compartment appear to be less organized and moving away form a normal appearance and moving towards a cancerous appearance. An index of several markers can be developed in order to make a determination that the patient is better, worse or unchanged.

The marker can be TGF-β and an increase in TGF-β can indicate that the patient is worse. The marker can be estrogen receptor and a decrease in presence of estrogen receptor can indicate that the patient is worse. The marker can be neoplastic cells and a change in cellular stage ranging from hyperplasia to invasive carcinoma indicates that the patient is worse. For example, where the cells are first hyperplastic and later atypically hyperplastic, the patient is worse; where the cells are first atypically hyperplastic and then at a later time ductal carcinoma in situ is identified in the cells, the patient is worse. Likewise, where a patient has high grade ductal carcinoma in situ at a first time, and at a later time, only atypically hyperplastic cells are detected, the patient has improved.

Concurrent with monitoring, and/or after a comparison is made between a marker at a first time and one at a later time, a treatment course can be begun and/or continued. Where a patient being monitored receives a determination that the patient is better, worse or unchanged, the treatment for that patient can be changed or kept the same. Thus, for any given result in the monitoring process, a treatment decision can be made. Such treatment decisions can include e.g. a recommendation to stop therapy or a recommendation to change the therapy. Changing the therapy can include, e.g. changing drug being administered (e.g. switching from one estrogen activity modulator to another, or switching from an estrogen activity modulator to another different class of drug), or changing (e.g. increasing or decreasing) a dosage of the drug being administered (e.g. increasing or decreasing the dose of an estrogen activity modulator that is being administered). In all cases a patient can be further monitored at later or regular intervals (i.e. periodically) for progress or regress of the cancer or precancer. See Table II for examples of prophetic monitoring results coupled to exemplary treatment recommendations. See also Table I below for exemplary examination and treatment of hypothetical asymptomatic patients.

TABLE I

Identification & Treatment

| patient | analyte | cytology | ERICA | diagnosis | SERM | dosage |
|---------|---------|----------|-------|-----------|------|--------|
| A | NAF right & left | right breast = ADH + | ER ++++ | ADH lesion right breast | tamoxifen | 1/10 of 20 mg (2 mg) systemic dosage-administered daily in a cream on the right nipple surface |
| B | ductal lavage of all ducts of the left breast | duct #3 = LG-DCIS + duct #5 = ADH + | duct #3 = ER ++ duct #5 = ER +++ | ADH lesions in left breast ducts #3, #5 | ioxdroxifene | time release capsule containing SERM placed in duct #3 and duct #5 once a month |
| C | NAF right and left breast | left breast = LG-DCIS + | ER ++ | LG-DCIS lesion(s) in left breast | faslodex | systemic oral admin. @ standard dosage |
| D | NAF followed by lavage and analysis of all ducts of right and left breasts | left breast, duct #6 = ADH + right breast, duct #2 = ADH + | L-duct #6 = ER +++++ R-duct #2 ER ++++ | ADH lesions in L-duct #6 and R-duct #2 | droloxifene and R-duct | small semi-permanent tubes placed in L-duct #6 #2 for daily admin. of |

TABLE I-continued

Identification & Treatment

| patient | analyte | cytology | ERICA | diagnosis | SERM | dosage |
|---|---|---|---|---|---|---|
| E | NAF followed by lavage and analysis of all ducts of right and left breasts | left breast, duct #7 = ADH + right breast, duct #4, 5 = LG-DCIS + | L-duct #7 = ER ++++ R-duct #4 = ER +++ R-duct #5 = ER ++ | lesions in L-duct #7, and R-duct #4, #5 | raloxifene | 1/10 systemic dose in a liquid suspension weekly placement of time release capsule in each of the 3 positive ducts; capsule strength for duct #5-3X dosage; duct #4-2X and duct #7-1X |

TABLE II

Treatment & Monitoring

| # | breast/ duct | EAM | Markers | Value | Later Value | Monitoring Frequency | Recommendation |
|---|---|---|---|---|---|---|---|
| 231 | L-2 | tamoxifen systemic dose at 50% of max dose | ER neoplasia | ER ++++ ADH | ER ++++ H | 3 months | keep treatment unchanged; check every 3 months; stop treatment when cells regress to normal |
|  | L-4 | — | ER neoplasia | ER ++++ H | ER ++++ normal | 3 months | — |
|  | R-3 | — | ER neoplasia | ER +++ LG-DCIS | ER ++++ ADH | 3 months | — |
|  | R-6 | — | ER neoplasia | ER ++++ ADH | ER ++++ H | 3 months | — |
| 243 | L-3 | raloxifene intraductal @ 20% of max systemic dose | TGF-β neoplasia | TGF-β neg. ADH | TGF-β neg. ADH | 2 months | keep treatment unchanged; check every 2 months; stop treatment when cells regress to normal |
|  | R-4 | raloxifene intraductal @ 20% of max systemic dose | TGF-β neoplasia | TGF-β neg. LG-DCIS | TGF-β neg. ADH | 2 months | keep treatment unchanged; check every 2 months; stop treatment when cells regress to normal |
| 253 | L-1 | genistein; intraductal @ 20% of max systemic dose | ER TGF-β neoplasia | ER +++ TGF-β neg. LG-DCIS | ER +++ TGF-β neg. LG-DCIS | 1 month | because condition unchanged after first month increase dosage to 20% of max systemic dosage |
| 253 | L-4 | genistein; intraductal @ 20% of max systemic dose | ER TGF-β neoplasia | ER ++ TGF-β low HG-DCIS | ER ++ TGF-β low HG-DCIS | 1 month | because condition unchanged after first month increase dosage to 20% of max systemic dosage |
|  | R-3 | genistein; intraductal @ 10% of max systemic dose in each duct | ER TGF-β neoplasia | ER ++ TGF-β med. HG-DCIS | ER ++ TGF-β med. HG-DCIS | 1 month | because condition unchanged after first month increase intraductal dosage to 20% of max systemic dosage |
| 267 | L-4 | faslodex; intraductal @ 20% of max | ER TGF-β neoplasia | ER + TGF-β med. HG-DCIS | ER ++++ TGF-β neg. ADH | 4 month | continue therapy in L-4; monitor in 2 months |

TABLE II-continued

Treatment & Monitoring

| # | breast/ duct | EAM | Markers | Value | Later Value | Monitoring Frequency | Recommendation |
|---|---|---|---|---|---|---|---|
| | R-4 | faslodex; intraductal @ 20% of max systemic dosage in each duct | ER TGF-β neoplasia | ER ++ TGF-β low LG-DCIS | ER ++++ TGF-β neg. normal | 4 month | stop therapy; monitor in 2 months |
| | R-5 | faslodex; intraductal @ 20% of max systemic dosage in each duct | ER TGF-β neoplasia | ER +++ TGF-β neg. ADH | ER ++++ TGF-β neg. normal | 4 month | stop therapy; monitor in 2 months |
| 273 | L-2 | toremifene systemic at 50% of max dosage | neoplasia | ADH | H | 3 months | check in 1 month; stop therapy when L-2 and R-2 are normal |
| | L-3 | — | neoplasia | H | normal | 3 months | — |
| | R-2 | — | neoplasia | ADH | H | 3 months | — |
| 287 | L-3 | GnRHA intraductal @ 20% of max dosage | ER neoplasia | ER +++ ADH | ER ++++ normal | 2 months | stop therapy in L-3; check every 2 months for 6 months |
| | R-7 | GnRHA intraductal @ 20% of max dosage | ER neoplasia | ER ++ HG-DCIS | ER +++ ADH | 2 months | continue therapy; check in 2 months; stop therapy when cells are normal and monitor |
| 291 | L-5 | tamoxifen systemic max systemic dosage | ER TGF-β neoplasia | ER ++ TGF-β low HG-DCIS | ER + TGF-β med. HG-DCIS | 2 months | change to faslodex-intraductal delivery @ 50% max systemic dosage |
| 295 | L-3 | tamoxifen systemic dose @ 100% max systemic dosage | ER TGF-β neoplasia | ER +++ TGF-β low ADH | ER ++ TGF-β med. LG-DCIS | 3 months | change to faslodex-systemic dosage @ 100% of max systemic dosage |
| | R-2 | — | ER TGF-β neoplasia | ER ++ TGF-β med. LG-DCIS | ER ++ TGF-β high HG-DCIS | 3 months | — |
| | R-4 | — | ER TGF-β neoplasia | ER +++ TGF-β neg. ADH | ER ++ TGF-β low LG-DCIS | 3 months | — |

Key:
ER = estrogen receptor; ADH = atypical ductal hyperplasia; H = hyperplasia; LG-DCIS = low grade ductal carcinoma in situ; HG-DCIS = high grade ductal carcinoma in situ; L = left breast; R = right breast

EXAMPLES

1. Diagnosis of ADH Lesion From Duct Fluid Retrieved From NAF

The right nipple of a female patient is placed under a vacuum breast pump and nipple aspirate fluid (NAF) is collected from the surface of the nipple. The fluid is analyzed by a local cytology laboratory. Upon the finding of ADH positive cells, a population of ductal epithelial cells is further analyzed by an ER-ICA test available from Abbott laboratories for estrogen receptor. The staining is also quantified for estrogen receptor to establish a level at the time of initial identification. The patient is tested for TGF-β levels in the ductal fluid to establish a base-line or reference level for later testing of TGF-β levels.

2. Treatment With Tamoxifen

A patient having an ADH lesion in a single breast milk duct on her right breast is treated by intraductal cannulation and delivery of tamoxifen weekly. The dosage is 1/10 of the systemic dosage that would be given (weekly) were she receiving a systemic dose. Once a month cells from the duct are retrieved in the ductal fluid prior to each administration, and these cells are examined for cytological characteristics and an ER-ICA test is performed on a portion of the cells. Records are kept. Every 3 months the ductal fluid is also analyzed for presence of TGF-β in the ductal fluid and in association with the ductal epithelial cells by standard ELISA assay. These levels are also noted. Upon significant increase in TGF-β levels, the SERM treatment is discontinued. However, the treatment can be discontinued earlier where cytology indicates that the lesions no longer exist in the ducts, e.g. where no abnormal cytology is detectable in the ductal epithelial cells from the affected duct. Upon such a finding, NAF fluid is also collected from both breasts to test the entire ductal networks of both breasts for the fluid and cell characteristics (cytology, ER tests and TGF-β) at the time of discontinuance of SERM treatment.

3. Identification of Asymptomatic Patients Ripe for Therapy With an Estrogen Activity Modulator A patient population of women is screened by testing negative with mammography. Ductal fluid from these women is collected by nipple aspiration and ducts that yield fluid are marked for later access. The pooled collected fluid is placed on at least one slide and stained and analyzed by cytology. The results of the analysis are recorded and the slides saved. The cytology of the nipple aspiration procedure is used to confirm or support later lavage results. The patient is scheduled for a lavage procedure of the ducts that yielded fluid in the nipple aspiration. The marked ducts of these patients are lavaged with a catheter infusing lavage fluid and ductal fluid mixed with the lavage fluid is retrieved from these ducts and kept separate so that a duct specific analysis can be made. Cells are separated from the fluid retrieved from the lavage procedure and placed on filters for analysis. Some cells are placed on slides for other tests. The cells on the filters are analyzed by cytology. Cells on one slide are analyzed by ER-ICA test for the presence and quantitation of estrogen receptors in the ductal epithelial cells, cells on another slide are analyzed by antibody staining for the presence of TGF-β.

Patients' ducts are scored on an index. The index includes cell stage, estrogen receptor quantitation and TGF-β presence. Patients having a neoplastic cell stage including hyperplasia, atypical ductal hyperplasia, low grade ductal carcinoma in situ, high grade ductal carcinoma in situ or invasive carcinoma receive a score of 1 to 5 depending on the severity (1=hyperplasia). Estrogen receptor scoring is made as described by the kit directions from the ER-ICA tests available from Abbott laboratory (Abbott Park, IL 60064—phone 800-323-9100) indicating % of cells stained. Less than 20% received a score of 10, 20% to 29% receives a score of 9, 30% to 39% receives a score of 8, 40% to 49% receives a score of 7, 50% to 59% receives a score of 6, 60% to 69% receives a score of 5, 70% to 79% receives a score of 4, 80% to 89% receives a score of 3, 90% to 99% receives a score of 2, and 100% receives a score of 1. The TGF-β scoring is 1 for TGF-β negative, 2 for low levels of TGF-β, 3 for medium levels of TGF-β, and 4 for high levels of TGF-β. A low score on the index will indicate a precancer. A high score will indicate a cancer. The lowest score possible given the presence of hyperplasia only, is around 1(hyperplasia)+1(100% ER staining)+1(negative TGF-β)=3. A high score might be 5 (invasive carcinoma)+10 (ER negative or less than 20% staining in an ER-ICA test)+4 (high levels of TGF-β)=19. Patients determined to have a score between 1 and 17 are considered ripe for treatment with an estrogen activity modulator. Because the ducts in which any neoplasia is occurring have been identified, the patient has the option of intraductal treatment. Practitioners and patients can select from amongst many available estrogen activity modulators for treatment. Monitoring of the patient on a periodic basis is recommnended.

4. Monitoring Patients Receiving Estrogen Activity Modulators

A patient population identified in example 3 is monitored during treatment by estrogen activity modulators. The estrogen activity modulator can be, e.g. tamoxifen, faslodex, toremifene, genistein, GnRHA, or others listed herein. The patient can be monitored using an index that includes some or all of such parameters as e.g. neoplastic cell stage progression (towards cancer) or regression (towards normal), estrogen receptor levels, TGF-β levels, maspin levels, CEA levels, PSA levels, GCDFP-15 levels, LDH levels, cytokeratin 19 levels, KLK3 (prostate specific antigen) levels, progesterone receptor levels, c-erbB2 levels, pS2 levels, cathepsin B levels, tumor associated antigen CA 15-3, p53 levels, levels of markers of angiogenesis, levels of markers of cell adhesion, levels or markers of invasion, or chromosomal abnormality. Any or all of these markers may be used in an index to monitor the patient.

The periodicity of monitoring can be selected by a practitioner based on the seriousness of the patient condition: the more serious the patient condition, the shorter the period between monitoring. Thus, for example a patient with a score above 15 from example 3, may be monitored biweekly; and a patient having a score between 1 and 5 may be monitored monthly, bimonthly, or every 3 months, etc.

Upon regression of the disease (e.g. regression in neoplastic cell stage and/or other marker indicators that the patient is improving), a practitioner can decide to reduce a dosage of the estrogen activity modulator. Such a decision to reduce a dosage should be followed by a period of close monitoring (e.g. every testing every two weeks) to ensure that such a reduction in dosage does not allow the cancer or precancer to progress. Otherwise, improvement in patient status can signal to a practitioner to keep the patient on the same treatment course, with the same drug and same dose, at least until no signs of cancer or precancer exist. Where the drug is administered intraductally, treatments can be stopped in each duct as it heals.

Upon no change in the disease, the practitioner can determine to increase a dosage of the drug or change to a new drug. The longer a period of no change has occurred, the more likely a practitioner will determine that the drug dosage should be increased, or the drug should be changed.

Upon progression of the precancer or cancer, or identification of new neoplastic conditions in new ducts, the practitioner can decide to increase a dosage of the drug, or change to a new drug. A patient who is not improving should be monitored very closely (e.g. weekly or biweekly) so that an effective drug and dosage can be found. In some cases a practitioner can combine more than one estrogen activity modulator, e.g. where there is reason to believe that a particular combination would be effective.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for risk reduction or therapeutic treatment of an asymptomatic patient at risk for developing breast cancer, said method comprising:

introducing a tool having a lumen sized for receiving ductal epithelial cells into a duct of a breast of the patient;

obtaining a ductal fluid sample comprising ductal epithelial cells from within said duct using said tool;

examining said ductal fluid sample collected from said duct to determine the presence of precancerous or cancerous ductal epithelial cells;

intraductally administering an estrogen activity modulator to a patient having precancerous or cancerous ductal epithelial cells through a ductal opening of the duct of the patient determined to include the precancerous or cancerous ductal epithelial cells.

2. A method as in claim 1, wherein a determination of the presence of precancerous or cancerous ductal epithelial cells is made from analysis of fluid comprising ductal epithelial cells that is collected from the milk duct of a breast of the patient.

3. A method as in claim 2, wherein the fluid collected is from a single duct.

4. A method as in claim 1, wherein whether precancerous or cancerous ductal epithelial cells are present is determined by cytological analysis of the ductal epithelial cells.

5. A method as in claim 1 or 4 further comprising detecting the presence of estrogen receptor in the ductal epithelial cells.

6. A method as in claim 1, 4 or 5, further comprising detecting the absence of TGF-β in the ductal fluid.

7. A method as in claim 1 or 4 wherein examining the ductal fluid comprises detection of a change in a level of a marker selected from the group consisting of carcinoma embryonic antigen (CEA), prostate specific antigen (PSA), Erb B2 antigen, gross cystic disease fluid protein-15 (GCDFP-15), and lactose dehydrogenase (LDH) in the ductal fluid.

8. A method as in claim 1 or 4 wherein examining the ductal fluid comprises detecting a chromosomal abnormality in the ductal epithelial cells.

9. A method as in claim 1, wherein the estrogen activity modulator comprises a class of agents selected from the group consisting of a selective estrogen receptor modulator (SERM), an estrogen antagonist, and a modulator of estrogen synthesis.

10. A method as in claim 1, wherein the estrogen activity modulator comprises an agent selected from the group consisting of tamoxifen, raloxifene, EM 800, droloxifene, ioxdroxifene, RU 39411, RU 58668, ICI 164384, faslodex, soy, a soy isoflavone, a gonadotropin releasing hormone agonist, and an aromatase inhibitor.

11. A method as in claim 10, wherein the estrogen activity modulator comprises a soy isoflavone, and the soy isoflavone is genistein or daidzein.

12. A method as in claim 10, wherein the estrogen activity modulator comprises an aromatase inhibitor, and the aromatase inhibitor is toremifene.

13. A method of treating an asymptomatic patient who has a likelihood of benefiting from the administration of an estrogen activity modulator for risk reduction or therapeutic treatment of breast cancer, said method comprising:

introducing a tool having an internal lumen sized for receiving ductal epithelial cells into a duct of a breast of the patient;

obtaining a ductal fluid sample including ductal epithelial cells from within said duct using said tool;

examining said ductal fluid sample collected from said duct to determine the presence of precancerous or cancerous ductal epithelial cells;

identifying the patient as likely to benefit from administration of an estrogen activity modulator based on the presence of either precancerous or cancerous ductal epithelial cells in said ductal fluid sample;

positioning a member through a ductal opening and within a breast duct of the patient based the identifying step; and intraductally administering the estrogen activity modulator using said member extending within the identified breast duct.

14. A method as in claim 13, wherein the intraductal administration comprises a delivery means selected from the group consisting of intraductal cannulation, intraductal catheterization, intraductal delivery of a time release capsule, intraductal delivery to a lactiferous sinus of the duct, and intraductal installment of a pump for delivering the agent into the duct.

15. A method as in claim 13, wherein the estrogen activity modulator comprises a class of agents selected from the group consisting of a selective estrogen receptor modulator (SERM), an estrogen antagonist, and a modulator of estrogen synthesis.

16. A method as in claim 13, wherein the estrogen activity modulator comprises an agent selected from the group consisting of tamoxifen, raloxifene, EM 800, droloxifene, ioxdroxifene, RU 39411, RU 58668, ICI 164384, faslodex, soy, a soy isoflavone, a gonadotropin releasing hormone agonist, and an aromatase inhibitor.

17. A method as in claim 13, wherein identifying the patient comprises identifying at least one specific duct having precancerous or cancerous ductal epithelial cells, and further wherein administering the estrogen activity modulator intraductally comprises intraductal administration to the specific duct.

18. A method of treating an asymptomatic patient who has a likelihood of benefiting from the administration of an estrogen activity modulator for risk reduction or therapeutic treatment of breast cancer, said method comprising:

introducing a tool having an internal lumen sized for receiving ductal epithelial cells into a duct of a breast of the patient;

lavaging said duct;

obtaining a ductal fluid sample including ductal epithelial cells from within said duct through said tool;

examining said ductal fluid sample collected from said duct to determine the presence of precancerous or cancerous ductal epithelial cells;

intraductally administering an estrogen activity modulator through a ductal opening of a breast duct of a patient having precancerous or cancerous ductal epithelial cells.

19. The method of claim 18 wherein the step of lavaging a duct of a breast of the patient comprises:

introducing lavage fluid into said duct through said tool, and wherein said obtaining step is performed after said lavaging step.

20. The method of claim 18 wherein said tool includes a tube comprising a port opening.

21. The method of claim 18 wherein said step of administering comprises repeatedly administering the estrogen activity modulator using a member that extends into said duct, said member being in place in said duct between each administration of the estrogen activity modulator.

22. The method of claim 18 wherein said tool includes a single lumen tube.

23. The method of claim 22 wherein said lavaging comprises introducing lavage fluid into said duct and collecting ductal fluid from said duct through said single lumen tube.

24. The method of claim 1 wherein said tool includes a tube comprising a port opening.

25. The method of claim 1 wherein said step of administering comprises repeatedly administering the estrogen activity modulator using a member that extends into said duct, said member being in place in said duct between each administration of the estrogen activity modulator.

26. The method of claim 13 wherein said tool includes a tube comprising a port opening.

27. The method of claim 13 wherein said step of administering comprises repeatedly administering the estrogen activity modulator using said member that extends into said duct, said member being in place in said duct between each administration of the estrogen activity modulator.

* * * * *